United States Patent [19]

Chen et al.

[11] Patent Number: 5,294,637
[45] Date of Patent: Mar. 15, 1994

[54] FLUORO TAXOLS

[75] Inventors: Shu-Hui Chen, Hamden; Vittorio Farina, West Hartford; Joydeep Kant, South Meriden; Dolatrai M. Vyas, Madison, all of Conn.

[73] Assignee: Bristol-Myers Squibb Company, New York, N.Y.

[21] Appl. No.: 62,687

[22] Filed: May 20, 1993

Related U.S. Application Data

[63] Continuation-in-part of Ser. No. 6,423, Jan. 19, 1993, abandoned, which is a continuation of Ser. No. 907,261, Jul. 1, 1992, abandoned, and a continuation-in-part of Ser. No. 996,455, Dec. 24, 1992, abandoned, and a continuation-in-part of Ser. No. 29,819, Mar. 11, 1993, Pat. No. 5,254,580.

[51] Int. Cl.$^5$ .................. A01N 43/02; C07D 305/00
[52] U.S. Cl. ............................ 514/449; 549/510; 549/511
[58] Field of Search ............... 514/449; 545/510, 511

[56] References Cited

U.S. PATENT DOCUMENTS

| | | | |
|---|---|---|---|
| 4,814,470 | 3/1989 | Colin et al. | 549/510 |
| 4,876,399 | 10/1989 | Holton et al. | 549/214 |
| 4,960,790 | 10/1990 | Stella et al. | 549/510 |
| 5,015,744 | 5/1991 | Holton et al. | 549/510 |
| 5,136,060 | 8/1992 | Holton et al. | 549/512 |

FOREIGN PATENT DOCUMENTS

| | | | |
|---|---|---|---|
| 400971A2 | 12/1990 | European Pat. Off. | 549/510 |
| 522958A1 | 1/1993 | European Pat. Off. | 549/510 |
| 524093A1 | 1/1993 | European Pat. Off. | 549/510 |
| 534707A1 | 3/1993 | European Pat. Off. | 549/510 |
| 534708A1 | 3/1993 | European Pat. Off. | 549/510 |
| 534709A1 | 3/1993 | European Pat. Off. | 549/510 |
| WO93/02064 | 2/1993 | PCT Int'l Appl. | 549/510 |
| WO93/06079 | 4/1993 | PCT Int'l Appl. | 549/510 |
| WO93/06093 | 4/1993 | PCT Int'l Appl. | 549/510 |
| WO93/06094 | 4/1993 | PCT Int'l Appl. | 549/510 |

OTHER PUBLICATIONS

S. Cai, et al, "Application of Protease-Catalyzed Regioselective Esterification in Synthesis of 6'-Deoxy-6'-fluoro- and 6-Deoxy-6-fluorolactosides", J. Org. Chem., 57, No. 12, pp. 3431–3437, 1992.

(List continued on next page.)

Primary Examiner—James H. Reamer
Attorney, Agent, or Firm—William T. Han

[57] ABSTRACT

This invention relates to a fluorinated taxol of formula I

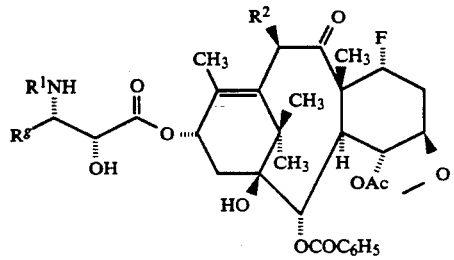

in which
$R^1$ is —$COR^z$ in which $R^z$ is RO— or R;
$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;
$R^2$ is —OCOR, H, OH, —OR, —$OSO_2R$, —OCON-$R^oR$, —OCONHR, —$OCOO(CH_2)_tR$, or —O-COOR; and
R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Further provided by this invention are pharmaceutical formulations and useful intermediates for the fluorinated taxols of formula I. A method of treating mammalian tumors using a compound of formula I is also provided.

13 Claims, No Drawings

OTHER PUBLICATIONS

G. I. Georg, et al, "Synthesis of Biologically Active Taxol Analogues with Modified Phenylisoserine Side Chains", Journal Of Medicinal Chemistry, 35, pp. 4230–4237, 1992.

G. I. Georg, et al, "Semisynthesis and Biological Activity of Taxol Analogues: Baccatin III 13-(N-benzoyl-(2'R,3'S)-3'-(p-tolyl)isoserinate), Baccatin III 13-(N-(p-toluoyl)-(2'R,3'S)-3'-phenylisoserinate), Baccatin III 13-(N-benzoyl-(2'R,3'S)-3'-(p-trifluoromethylphenyl)isoserinate), and Baccatin III 13-(-N-(p-trifluoromethylbenzoyl)-(2'R,3'S)-e'--phenylisoserinate)", BIOORGANIC & MEDICAL CHEMISTRY LETTERS, 2, No. 12, pp. 1751–1754, 1992.

G. I. George, et al, "Novel Biologically Active Taxol Analogues: Baccatin III 13-(N-(p-Chlorobenzoyl-)-2'R,3'S)-3'-phenylisoserinate) and Baccatin III 13-(-N-Benzoyl-(2'R,3'S)-3'-(p-chlorophenyl)isoserinate)", BIOORGANIC & MEDICAL CHEMISTRY LETTERS, 2, No. 4, pp. 295–298, 1992.

F. Gueritte-Voegelein et al, "Relationships between the Structure of Taxol Analogues and Their Antimitotic Activity," JOURNAL OF MEDICINAL CHEMISTRY, 1991, 34, pp. 992–998.

D. G. I. Kingston, et al, "The Chemistry of Taxol, A Clinically Useful Anticancer Agent", JOURNAL OF NATURAL PRODUCTS, 53, No. 1, pp. 1–12, 1990.

N. F. Magri and D. G. I. Kingston, "Modified Taxols, 2.[1] Oxidation Products of Taxol", J. ORG. CHEM., 51, pp. 797–802, 1986.

N. F. Magri and D. G. I. Kingston, "Modified Taxols, 4. Synthesis and Biological Activity of Taxols Modified in the Side Chain", JOURNAL OF NATURAL PRODUCTS, 51, No. 2, pp. 298–306, 1988.

W. P. McGuire, M. D. et al., "Taxol: A Unique Antineoplastic Agent with Significant Activity in Advanced Ovarian Epithelial Neoplasms," ANNALS OF INTERNAL MEDICINE, Aug. 15, 1989, III, No. 4, pp. 273–279.

I. Ojima, et al., "Efficient and Practical Asymmetric Synthesis of the Taxol C-13 Side Chain, N-Benzoyl-(2R,3S)-3-phenylisoserine, and Its Analogues via Chiral 3-Hydroxy-4-aryl-$\beta$-lactams through Chiral Ester Enolate-Imine Cyclocondensation", J. ORG. CHEM., 56, pp. 1681–1683, 1991.

I. Ojima, et al., "New and Efficient Approaches to the Semisynthesis of Taxol and Its C-13 Side Chain Analogs by means of $\beta$-Lactam Synthon Method", TETRAHEDRON, 48, No. 34, pp. 6985–7012, 1992.

C. S. Swindell et al., "Biologically Active Taxol Analogues with Deleted A-Ring Side Chain Substituents and Variable C-2' Configurations," JOURNAL OF MEDICINAL CHEMISTRY, 1991, 34, pp. 1176–1184.

FLUORO TAXOLS

CROSS REFERENCE TO RELATED APPLICATIONS

This application is a continuation-in-part application of U.S. Ser. No. 08/006,423, filed Jan. 19, 1993 now abandoned, which is herein incorporated by reference in its entirety and which in turn is a continuation application of Ser. No. 07/907,261, filed Jul. 1, 1992 now abandoned. This is also a continuation-in-part application of U.S. Ser. Nos. 07/996,455 now abandoned, filed Dec. 24, 1992, and 08/029,819, filed Mar. 11, 1993, U.S. Pat. No. 5,254,580 both of which are herein incorporated by reference in their entirety.

FIELD OF INVENTION

The present invention provides compounds having antitumor activities. Also provided by this invention are intermediates for making compounds having antitumor activities.

BACKGROUND OF INVENTION

Taxol was first isolated from the stem bark of Western Yew, *Taxus brevifolia* Nutt (Taxaceae) and has the following structure (with the 2'-, 7-, 10- and 13th-positions indicated)

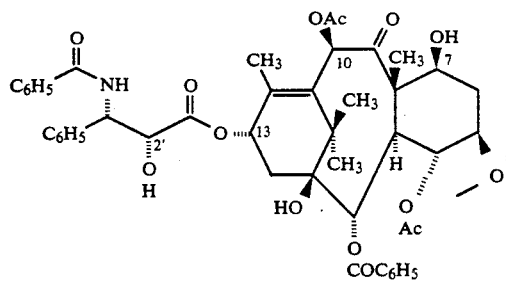

In clinical trials sponsored by the National Cancer Institute (NCI), taxol has shown promising results in fighting advanced cases of ovarian, breast, and other cancers. Taxol has recently been approved for the treatment of metastatic carcinoma of the ovary.

Taxol is unique among antimitotic drugs in that it promotes the assembly of stable microtubules from tubulin even under otherwise unfavorable conditions. The drug binds to microtubules, stabilizing them from depolymerization, thus disrupting the tubulinmicrotubule equilibrium and consequently inhibiting mitosis. The mechanism of action, toxicology, clinical efficacy, etc. of taxol are reviewed in a number of articles, such as in an article by Rowinsky et al. in Taxol: A Novel Investigational Antimicrotubule Agent, *J. Natl. Cancer Inst.*, 82: p 1247 (1990).

Since the discovery of significant effectiveness in cancer treatment, many laboratories have launched programs to design taxol analogues in search of better pharmacological profiles. Out of such a program was the discovery of taxotere of the formula

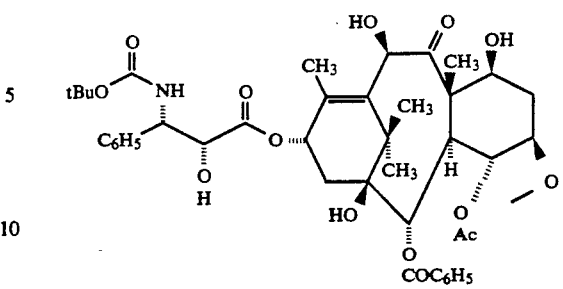

which has been reported to be as effective as taxol at promoting the assembly of microtubules and approximately twice as cytotoxic. See, Biologically Active Taxol Analogues with Deleted A-Ring Side Chain Substitutents and Variable C-2' Configurations, *J. Med. Chem.*, 34, p 1176 (1991); Relationships between the Structure of Taxol Analogues and Their Antimitotic Activity, *J. Med. Chem.*, 34, p 992 (1991).

In recent years, the introduction of fluorine into pharmacologically active compounds has led to the discovery of some profound and unexpected results. (For a comprehensive review on the advances in the preparation of biologically active organofluorine compounds, see: Advances in the Preparation of Biologically Active Organofluorine Compounds, *Tetrahedron*, 43, No. 14, p 3123 (1987).) It is the intention of the present invention to provide fluorinated taxols and their derivatives.

SUMMARY OF INVENTION

This invention relates to a fluorinated taxol derivative of formula I

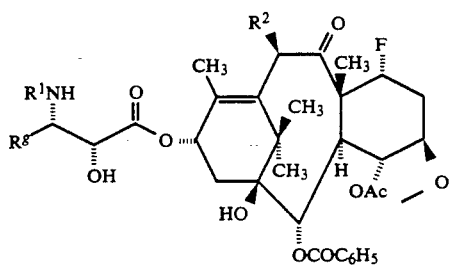

in which $R^1$ is —$COR^z$ in which $R^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^2$ is —OCOR, H, OH, —OR, —$OSO_2R$, —OCON$R^oR$, —OCONHR, —OCOO$(CH_2)_tR$, or —OCOOR; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Further provided by this invention are pharmaceutical formulations and useful intermediates for the fluorinated taxols of formula I. A method of treating mammalian tumors using a compound of formula I is also provided.

DETAILED DESCRIPTION OF INVENTION

This invention relates to a fluorinated taxol derivative of formula I

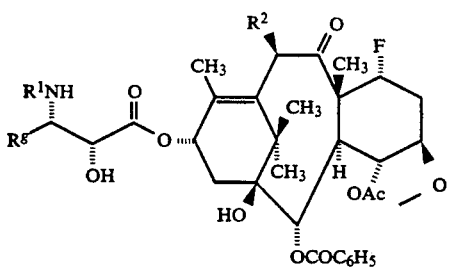

in which

R$^1$ is —COR$^z$ in which R$^z$ is RO— or R;

R$^g$ is C$_{1-6}$ alkyl, C$_{2-6}$ alkenyl, C$_{2-6}$ alkynyl, C$_{3-6}$ cycloalkyl, or a radical of the formula —W—R$^x$ in which W is a bond, C$_{2-6}$ alkenediyl, or —(CH$_2$)$_t$—, in which t is one to six; and R$^x$ is naphthyl, furyl, thienyl or phenyl, and furthermore R$^x$ can be optionally substituted with one to three same or different C$_{1-6}$ alkyl, C$_{1-6}$ alkoxy, halogen or —CF$_3$ groups;

R$^2$ is —OCOR, H, OH, —OR, —OSO$_2$R, —OCONR$^o$R, —OCONHR, —OCOO(CH$_2$)$_t$R, or —OCOOR; and R and R$^o$ are independently C$_{1-6}$ alkyl, C$_{2-6}$ alkenyl, C$_{3-6}$ cycloalkyl, C$_{2-6}$ alkynyl, or phenyl, optionally substituted with one to three same or different C$_{1-6}$ alkyl, C$_{1-6}$ alkoxy, halogen or —CF$_3$ groups The synthesis of a fluorinated taxol derivative of formula I can be accomplished by a wide variety of methods. The synthetic descriptions and specific examples that follow are intended only for the purpose of illustration, and are not to be construed as limiting in any manner to make compounds of the present invention by other methods.

In one embodiment, a process of Scheme I may be employed to make a compound of formula I. In Scheme I, 2'-hydroxy protected taxol of formula II is reacted with diethylaminosulfur trifluoride (DAST) to afford 7-α-fluorotaxol derivative of formula III in addition to 8-desmethyl-7,8-cyclopropataxol (or simply 7,8-cyclopropataxol) derivative of formula XXV. Step (a). The reaction of Step (a) can be run in a variety of solvents, such as tetrahydrofuran, methylene chloride, diethyl ether, toluene, 1,1-dimethoxyethane (DME), etc., or any combination/mixture thereof. It has been generally observed, when Step (a) is conducted in a mixture of THF/diethyl ether or about 10:1 to 8:1 of toluene to tetrahydrofuran, higher ratio of 7-α-fluorotaxol III to 7,8-cyclopropataxol XXV can be obtained. As used herein, R$^3$ is a conventional hydroxy protecting group. A compound of formula III may be separated from compound XXV, or the mixture may be used in Step (b) without any separation, and product I$^1$ separated from compound XXVI after Step (b). The separation of the compounds can be effected by any conventional purification technique normally employed by a person skilled in the art. The separation methods include chromatography, fractional crystallization, etc. A particularly suitable method for the separation is HPLC (High Pressure Liquid Chromatography).

As used herein, conventional hydroxy protecting groups (or simply hydroxy protecting groups) are moieties which can be employed to block or protect a hydroxy function, and they are well-known to those skilled in the art. Preferably, said groups are those which can be removed by methods resulting in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl (or simply trichloroethyloxycarbonyl), tetrahydropyranyl, tetrahydrofuranyl, t-butyl, benzyl, p-nitrobenzyl, p-methoxybenzyl, diphenylmethyl, triC$_{1-6}$alkylsilyl, triphenylsilyl, and the like. Other suitable protecting groups which may be used are found in Chapter 2 of "Protecting Groups in Organic Synthesis", Second Ed., by Theodora W. Greene and Peter G. M. Wuts (1991, John Wiley & Sons). A particularly advantageous protecting group for formula II compounds is benzyloxycarbonyl, which can be removed conveniently by catalytic hydrogenolysis, or triC$_{1-6}$alkylsilyl, which can be removed by fluoride ion.

In another embodiment, a compound of formula I$^2$ may be made by a process of Scheme II. In the Scheme, (C)13-side chain is removed reductively from a compound of formula I$^1$ by a reducing agent such as tetrabutylammonium borohydride to afford 7-α-fluoro baccatin III of formula IV. Step (a). Azetidinone XV is subsequently reacted with a compound of formula IV in Step (b). The general class of azetidinones of formula XV are well known. Their syntheses or syntheses of their precursors have been reported such as by Holton in European Patent Application 0,400,971 A2 published on Dec. 5, 1990; also by Holton in European Patent Applications 0,534,709 A1, 0,534,708 A1, and 0,534,707 A1 all published on Mar. 31, 1993; by Ojima et al. in Tetrahedron, 48, No. 34, pp 6985-7012 (1992); Journal of Organic Chemistry, 56, pp 1681-1683 (1991); and Tetrahedron Letters, 33, No. 39, pp 5737-5740 (1992); by Brieva et al. in J. Org. Chem., 58, pp 1068-1075; and by Palomo et al. in Tetrahedron Letters, 31, No. 44, pp 6429-6432 (1990); all nine disclosures are herein incorporated by reference in their entirety. The methods that can be adapted to variations in order to produce other azetidinones within the scope of formula XV, but not specifically disclosed herein or in the above nine references or reported elsewhere, will be obvious to anyone skilled in the art.

European Patent Applications 0,400,971 A2 0,534,709 A1, 0,534,708 A1, and 0,534,707 A1, and Tetrahedron, 48, No. 34, pp 6985-7012 (1992) also describe processes whereby the class of azetidinones of formula XV are reacted with (C)13-hydroxy group of baccatin III derivatives or metal alkoxide thereof to afford taxol analogues with a variety of (C)13-side chains. In Step (b) of Scheme II, it is advantageous to convert the hydroxy group on the (C)13-carbon (marked with the asterisk) into a metal alkoxide before the coupling. The metal cation of said metal alkoxide is preferably selected from Group Ia or IIa metals. The formation of a desired metal alkoxide may be done by reacting a compound of formula IV with a strong metal base, such as lithium diisopropylamide, C$_{1-6}$alkyllithium, lithium bis(trimethylsilyl)amide, phenyllithium, sodium hydride, potassium hydride, lithium hydride, or the like base. For example when lithium alkoxide is desired, a compound of formula IV may be reacted with n-butyllithium in an inert solvent such as tetrahydrofuran. Removal of R$^3$ from a compound of formula V in Step (c), affords a compound of formula I$^3$. When R$^3$ is a triC$_{1-6}$alkylsilyl group, such as triethylsilyl group, it can be removed by fluoride ion or with a mineral acid in alcohol or acetonitrile. The removal with fluoride ion is conducted in an inert solvent such as tetrahydrofuran, methylene chloride, 1,4-dioxane, DMF, chloroform, or in the like solvent; and preferably the reaction medium is buffered with a weak acid such as acetic acid. The presence of 7,8-cyclopropa derivative, if any, does not materially affect each step of Scheme II, provided that proper amounts of reagents which will be consumed by its presence will be taken into account. Normally it will be found preferable to separate the 7,8-cyclopropa derivative after Step (a) but before Step (b).

Scheme III describes a method to arrive at the compounds of formula $I^5$, in which $R^m$ is —OCOR, —OSO$_2$R, —OCONR$^o$R, —OCONHR, —OCOO(CH$_2$)$_t$R, or —OCOOR. The starting compounds of formula XXX are well described in the art or can be made by methods well known in the taxol art. For example, as shown in Scheme IIIa, a compound of formula XXXVIII can be reacted with RC(=O)L, R(CH$_2$)$_t$OC(=O)L, ROC(=O)L, LSO$_2$R, LCONR$^o$R, LCONHR, O=C=N—R or an anhydride derivative thereof, in which L is a typical leaving group such as chloro, bromo, mesyl, trifluoromethanesulfonyl, or tosyl, to afford a compound of formula XXXIX. A base is normally required in Step (a) to initially deprotonate proton from C-10 hydroxy group. A particularly useful base for Step (a) is a strong base such as $C_{1-6}$alkyllithium, lithium bis(trimethylsily)amide, or the like base used in about 1.1 equivalent amount. The deprotonation by base is preferably conducted in aprotic solvent, such as tetrahydrofuran, at low temperature, usually in the range from $-40°$ to $0°$ C. In Step (b), a compound of formula XXXIX can be reacted with an azetidinone of formula XV in a substantially identical manner to Step (b) of Scheme II to afford a compound of formula XL from which $R^3$ groups can be removed to afford a compound of formula XXX.

A compound of formula $I^3$, which is further within the scope of formula I compounds, may be made by a process of Scheme IV. In Step (a), when a compound of formula VI is treated with between one to two equivalents of a conventional hydroxy protecting reagent, preferably trichloroethyl chloroformate, a mixture of 2'- and 7-hydroxy protected (a compound of formula XIII) and 2'- and 10-hydroxy protected (a compound of formula VII) taxol derivatives may be simultaneously obtained.

A compound of formula XIII is subsequently reacted with 1,1,2-trifluoro-2-chlorotriethylamine in Step (b) to afford a dieneone of formula VIII. In Step (c), protecting groups $R^3$ are removed. (The removal of trichloroethyloxycarbonyl group can be done by zinc dust in acetic acid.) In Step (d), the diene of a compound of formula IX is catalytically hydrogenated to afford a compound of formula X. Subsequently in Step (e), 2'-hydroxy group is once again protected, this time preferably with benzyloxycarbonyl, to afford a compound of formula XI. Treating a compound of formula XI with DAST yields a fluoro compound of formula XII. Removal of protecting group $R^3$ in Step (g) affords a compound of formula $I^3$.

Scheme V describes a process for making a compound of formula $I^4$, which is further within the scope of formula I compounds. In Step (a), a compound of formula VII is reacted with DAST to afford a compound of formula XIV. Removal of $R^3$ protecting groups affords a compound of formula $I^4$.

A compound of formula VI is either already known or can be readily made by a process of Scheme VI. Step (a) is substantially identical to Step (b) of Scheme II. A baccatin III derivative of formula XXXIII with protecting groups on 7- and 10-hydroxy groups is also either already known or can be readily made from 10-deacetylbaccatin III. See for example, European Patent Applications 0,253,738,A1 and 0,522,958,A1, published Jan. 20, 1988 and Jan. 13, 1993, respectively. Removal of hydroxy protecting groups in Step (b) affords a compound of formula VI.

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; $C_{3-6}$ cycloalkyl refers to cyclopropyl, cyclobutyl, cyclopentyl, or cyclohexyl; $C_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; $C_{2-6}$ alkenediyl refers to groups such as ethylene-1,2-diyl (vinylene), 2-methyl-2-butene-1,4-diyl, 2-hexene-1,6-diyl, and the like groups; $C_{1-6}$ alkyloxy (alkoxy) refers to straight or branched alkyloxy group such as methoxy, ethoxy, n-propoxy, i-propoxy, n-butoxy, t-butoxy (t-butyloxy), n-pentyloxy, n-hexyloxy, or 3-methylpentyloxy, to name a few; and halogen refers to fluorine, chlorine, bromine, or iodine. Azetidinone refers to azetidin-2-one. In the instant application, all symbols once defined retain the same meaning until they are redefined.

SCHEME I

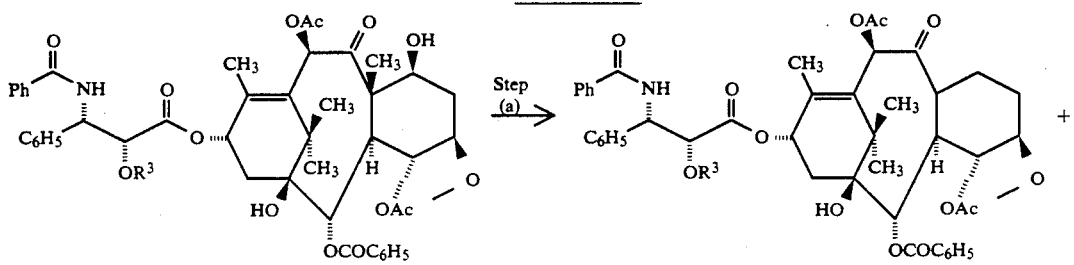

II            XXV

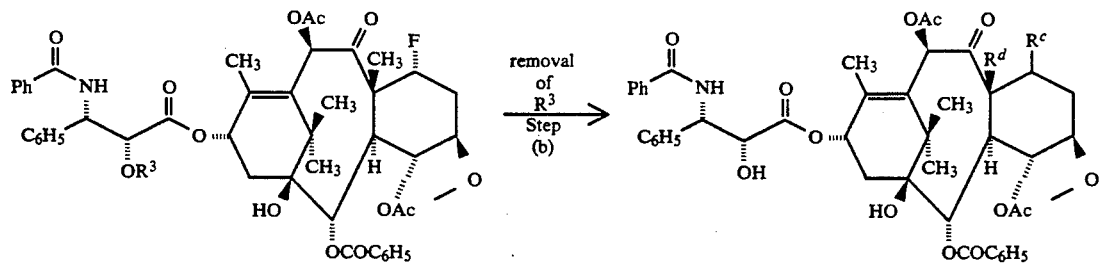
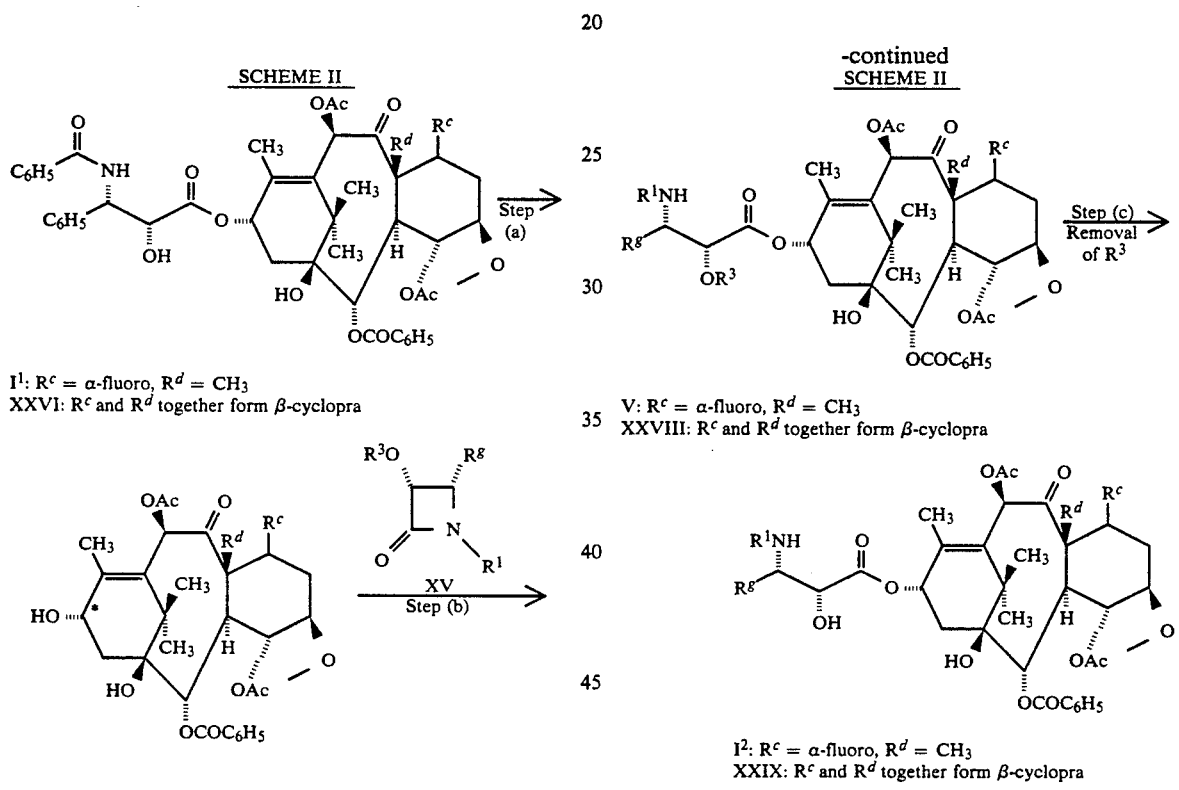
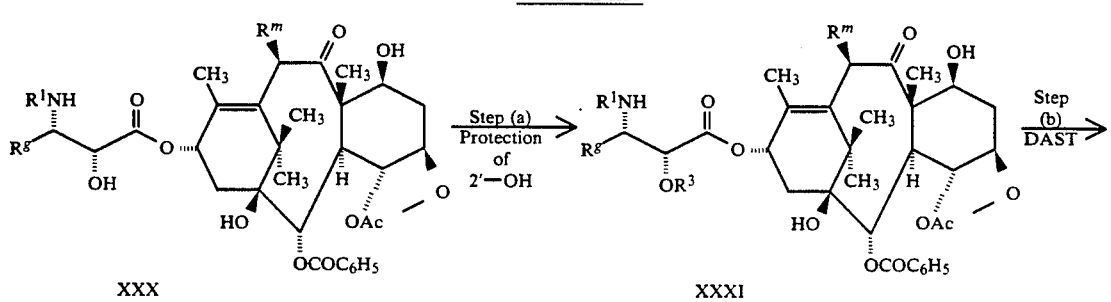

-continued
SCHEME III
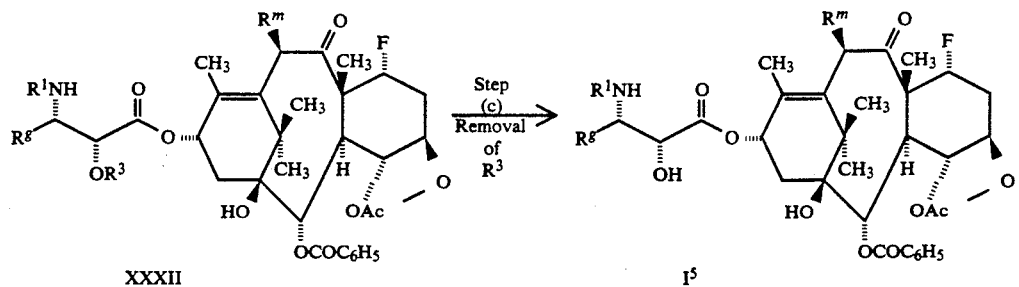
XXXII → I⁵ (Step (c) Removal of R³)
Scheme IIIa
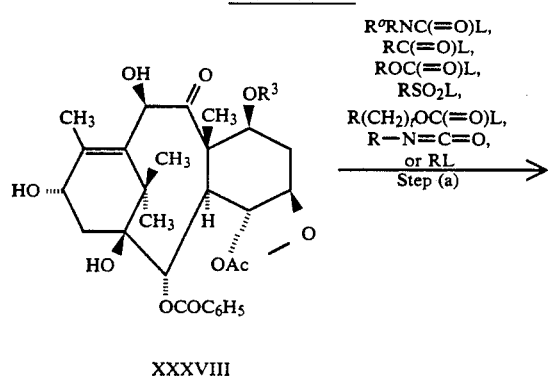
XXXVIII → XXXIX (Step (a), reagents: RᵒRNC(=O)L, RC(=O)L, ROC(=O)L, RSO₂L, R(CH₂)OC(=O)L, R—N=C=O, or RL)
-continued
Scheme IIIa
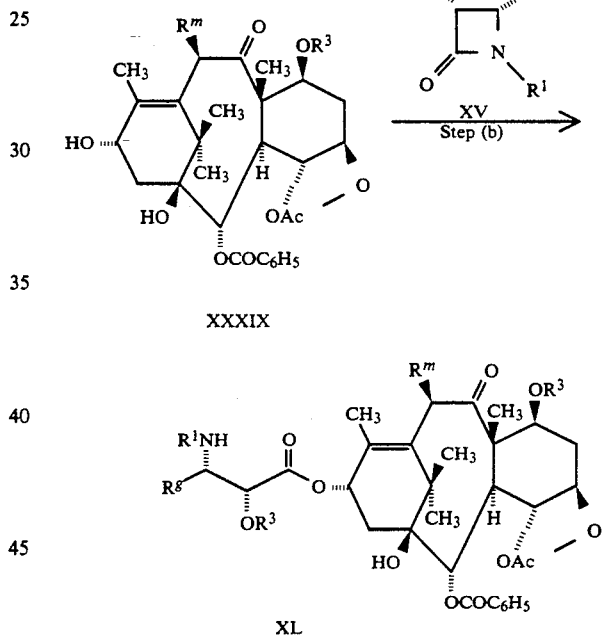
XXXIX → XL (Step (b), reagent XV)
SCHEME IV
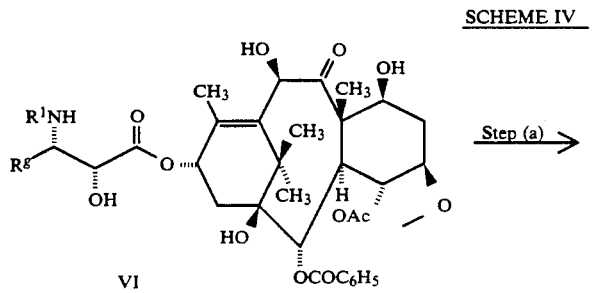
VI → Step (a)

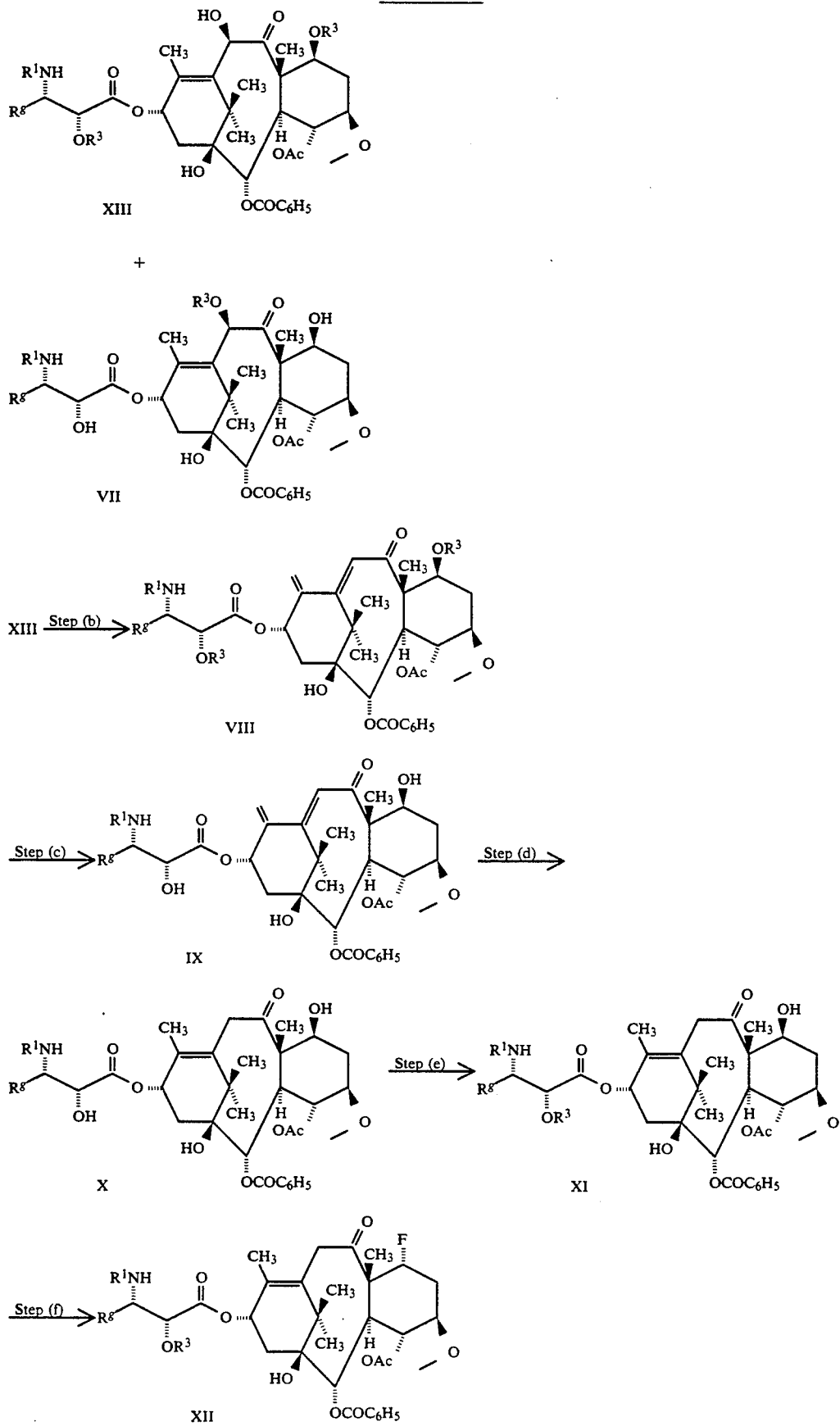

5,294,637
SCHEME IV -continued
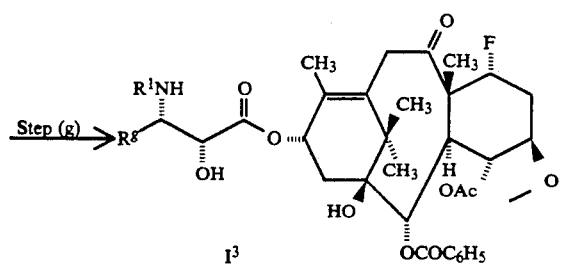
SCHEME V
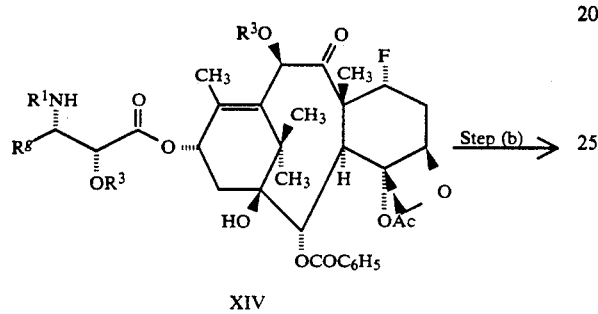
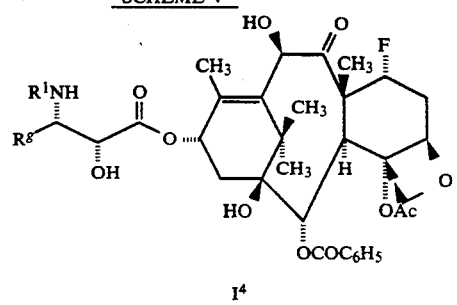
SCHEME VI
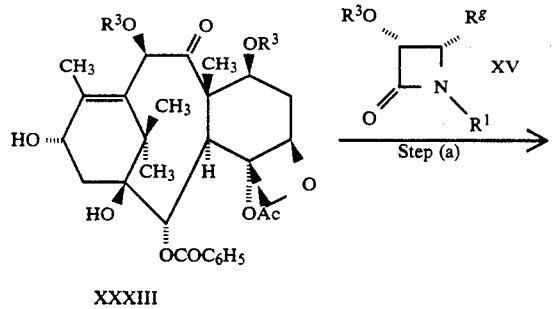
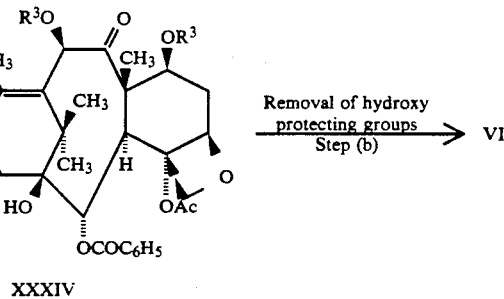
SCHEME VII
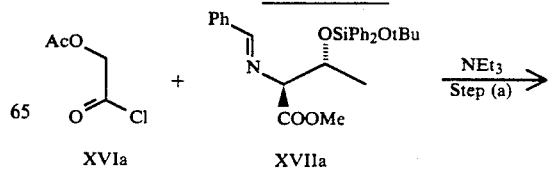

-continued
SCHEME VII

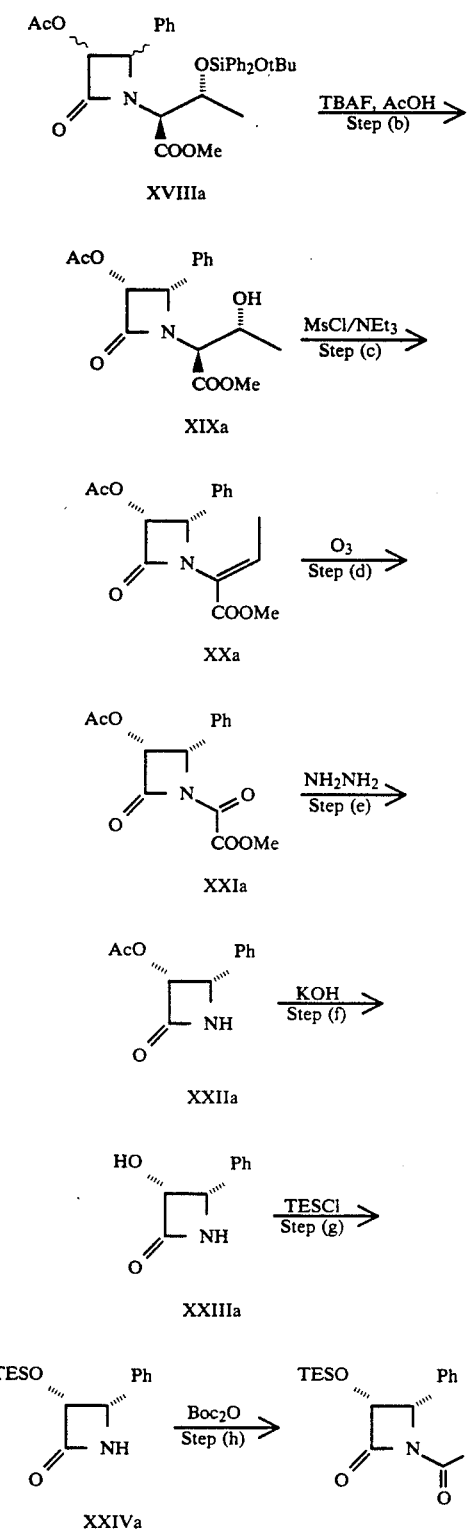

invention and are not to be construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad multiplet (bm), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. "Exch." means exchangeable with $CD_3OD$. (For example, "d plus exch." means a doublet plus an exchangeable signal. The total signal collapses to just a doublet after the other proton has been exchanged.) "Incl." means including.

The infrared (IR) spectral description includes only absorption wave numbers (cm$^{-1}$) having functional group identification value.

Celite is a registered trademark of the Johns-Manville Products Corporation for diatomaceuous earth.

The abbreviations used herein are conventional abbreviations widely employed in the art. Some of which are:

| | |
|---|---|
| Ac | acetyl |
| Ar | aryl |
| Bz | benzoyl |
| Cbz | benzyloxycarbonyl |
| DCI | desorption chemical ionization |
| DMF | dimethylformamide |
| DMSO | dimethyl sulfoxide |
| FAB | fast atom bombardment |
| h | hour(s) |
| HRMS | high resolution mass spectrometry |
| i-PrOH | isopropylalcohol |
| min | minute(s) |
| MS | mass spectrometry |
| NOBA | m-nitrobenzylalcohol |
| Ph | phenyl |
| rt | room temperature |
| tBu | tertiarybutyl |
| TES | triethylsilyl |
| THF | tetrahydrofuran |
| tlc | thin layer chromatography |
| v/v | volume/volume |
| Y | yield |

DESCRIPTION OF SPECIFIC EMBODIMENTS

The specific examples which follow illustrate the synthesis of representative compounds of the instant invention.

The Tables 1 and 2 list some compounds whose syntheses are described in the Examples below.

TABLE 1

| COMPOUND # | R¹ | Rᵃ | Rᵇ | Rᵉ |
|---|---|---|---|---|
| IIa | PhC(=O) | AcO | PhCH₂OC(=O) | β-OH |
| IIIa | PhC(=O) | AcO | PhCH₂OC(=O) | α-F |
| Ia | PhC(=O) | AcO | H | α-F |
| Va | tBuOC(=O) | AcO | Et₃Si | α-F |
| Ib | tBuOC(=O) | AcO | H | α-F |
| VIa | PhC(=O) | HO | H | β-OH |
| XIIIa | PhC(=O) | HO | Cl₃CCH₂OC(=O) | Cl₃CCH₂OCO— (β-isomer) |
| VIIa | PhC(=O) | Cl₃CCH₂OCO— | Cl₃CCH₂OC(=O) | β-OH |
| Xa | PhC(=O) | H | H | β-OH |
| XIa | PhC(=O) | H | PhCH₂OC(=O) | β-OH |
| XIIa | PhC(=O) | H | PhCH₂OC(=O) | α-F |
| Ic | PhC(=O) | H | H | α-F |
| Id | PhC(=O) | HO | H | α-F |
| XIVa | PhC(=O) | Cl₃CCH₂OCO— | Cl₃CCH₂OC(=O) | α-F |

TABLE 2

[Structure shown: taxol-derivative core with substituents R¹NH–CH(C₆H₅)–CH(OR^b)–C(O)–O– attached to the taxane ring system bearing CH₃ groups, =CH₂, OH, OAc, OCOC₆H₅, and OR^f]

| COMPOUND # | R¹ | R^b | R^f |
|---|---|---|---|
| VIIIa | PhC(=O) | Cl₃CCH₂OC(=O) | Cl₃CCH₂OC(=O) |
| IXa | PhC(=O) | H | H |

EXAMPLE 1

2'-O-(Benzyloxycarbonyl)taxol (IIa)

To a stirred solution of taxol (150 mg, 0.176 mmol) and N,N-diisopropylethylamine (93 μL, 0.534 mmol, 3 eq.) in anhydrous $CH_2Cl_2$ (4 mL) at room temperature was added benzyl chloroformate (75 μL, 0.525 mmol, 3 eq.) at room temperature. The reaction mixture was stirred at room temperature for 3 h. The reaction mixture was concentrated to 2 mL in volume and the product was purified on a silica gel column, using 1:1 of EtOAc/hexanes as eluant, to obtain 150 mg (0.152 mmol, Y:86%) of the title compound, IIa, as a white powder: mp, 140°–150° C. (decomposition); $[\alpha]_D^{20}$ −53.5° (c=0.2, 95% EtOH); ¹H-NMR (300 MHz, acetone-d₆) δppm: 1.18 (3H, s, 17-H₃), 1.92 (3H, s, 16-H₃), 1.66 (3H, s, 19-H₃), 1.96 (3H, s, 18-H₃), 2.16 (3H, s, 10-OAc), 2.5 (3H, s, 4-OAc), 3.53 (1H, d, J=5.89 Hz, 7-OH, exchanged with D₂O), 3.85 (1H, d, J=7.19 Hz, 3-H), 3.9 (1H, s, 1-OH, exchanged with D₂O), 4.17 (2H, ABq, 20-H₂), 4.25 (1H, m, 7-H), 4.97 (1H, d, J=9.56 Hz, 5-H), 5.19 (2H, ABq, OCH₂C₆H₅), 5.54 (1H, d, J=5.5 Hz, 2'-H), 5.68 (1H, d, J=7.13 Hz, 2-H), 6.01 (1H, dd, J=5.5, 9.05 Hz, 3'-H), 6.17 (1H, bt, J=9.0 Hz, 13-H), 6.42 (1H, s, 10-H), 7.28–7.69 (16H, m), 7.87 (2H, "d", J=8 Hz, 3'-NHCOPh), 8.14 (2H, "d", J=8 Hz, 2-CO₂Ph), 8.55 (1H, d, J=9.06 Hz, NH, exchanged with D₂O); MS (FAB-NOBA/NaI+KI): m/e 988 (M+H)⁺, 1010 (M+Na)⁺, 1026 (M+K)⁺; IR (KBr) νmax: 3448, 1748 (C=O), 1726 (CONH), 1250 (C—O) cm⁻¹; UV (MeOH:H₂O, 1:1) λmax: 198 (ε7.3×10⁴), 230 nm (ε2.7×10⁴).

HRMS calcd for $C_{55}H_{58}NO_{16}$ (MH+): 988.3756. Found: 988.3766.

Anal. calcd for $C_{55}H_{57}NO_{16} \cdot H_2O$: C, 65.67; H, 5.92; N, 1.40. Found: C, 65.99; H, 5.64; N, 1.33.

EXAMPLE 2

2'-O-Benzyloxycarbonyl-7-α-fluorotaxol (IIIa)

DAST (18.7 μL, 0.141 mmol) was dissolved in dry dichloromethane (0.5 mL), and this solution was cooled to 0° C. A solution of compound IIa (71 mg, 0.072 mmol) in dichloromethane (1 mL) was added and the resulting solution was kept at 0° C. for 30 min and at room temperature for 4 h. Then water (0.15 mL) was added to the reaction mixture in order to quench the reaction and the resultant mixture was concentrated to leave a residue. The residue was chromatographed on a silica gel column (being eluted with 40% ethyl acetate in hexane) to yield 61 mg of a mixture of compound IIIa and 2'-O-benzyloxycarbonyl-8-desmethyl-7,8-cyclopropataxol (XXVa); ¹H-NMR (mixture of IIIa and XXVa, CDCl₃) δ8.08 (d, J=8.7 Hz, 2H) 7.65–7.17 (m, 18H) 6.85 (exch. d, J=9.4 Hz, 1H) 6.49 (s, 1H, H-10) 6.25–6.14 (m, 1H, H-13) 5.92 (dd, J=9.4 Hz, J'=2.4 Hz, 1H, H-3') 5.68 (d, J=7.2 Hz, 1H, H-2) 5.38 (m, 1H, H-2') 5.06 (m 2H) 4.96 (bd, 1H, H-5) 4.80–4.35 (m, 1H, H-7) 4.31–4.20 (m, 2H, H-20) 3.94 (d, H=7.2 Hz, 1H, H-3) 2.47–1.64 (m, 17H incl. s at 2.38, 3H, at 2.11, 3H, at 1.78, 3H, 1.65, 3H) 1.10 (s, 3H) 1.07 (s, 3H).

EXAMPLE 3

7-α-Fluorotaxol (Ia)

A 1:1 mixture of compound IIIa and 2'-O-benzyloxycarbonyl-8-desmethyl-7,8-cyclopropataxol (89 mg) was dissolved in ethyl acetate (3 mL) and the mixture was stirred under slightly over one atmospheric pressure of hydrogen in the presence of palladium on charcoal (10% Pd, 29 mg, 0.027 mmol). After 12 h, the solvent was removed, and the residue was purified by silica gel chromatography (being eluted with 40% ethyl acetate in hexane) to afford 67.7 mg of the title compound, along with 8-desmethyl-7,8-cyclopropataxol (XXVIa), as a white solid; ¹H-NMR (mixture of XXVIa and Ia, CDCl₃) δ8.11 (d, J=8.7 Hz, 2H) 7.72–7.07 (m, 14H) 6.50 (s, 1H, H-10) 6.14 (bt, 1H, H-13) 5.80 (dd, J=9.0 Hz, J'=2.4 Hz, 1H, H-3') 5.74 (d, J=7.2, 1H, H-2) 4.98 (d, J=8.1 Hz, 1H, H-5) 4.77 (m, 1H, H-2') 4.70–4.40 (m, 1H, H-7) 4.40–4.21 (m, 2H, H-20) 4.02 (d, J=7.2 Hz, 1H, H-3) 2.60–1.55 (m, 17H, incl. s at 2.37, 3H, 2.20, 3H, 1.77, 3H, 1.74, 3H) 1.14 (s, 3H) 1.12 (s, 3H).

The following HPLC methods can be used to separate 7-α-fluorotaxol from 8-desmethyl-7,8-cyclopropataxol:

Method 1

| Equipment | |
|---|---|
| Pump: | PE Series 4 |
| Column: | Shandon Hypercarb (graphitized carbon), 7μ, 100 × 4.6 mm, #59864750 (information on preparative size columns may be obtained from Keystone Scientific, Bellefonte, PA) |
| Injector: | PE ISS-100 |
| Detector: | HP-1040M |
| Conditions | |
| Mobile Phase: | 85:15 methylene chloride: hexane Separation not lost at 80:19:1 methylene chloride: hexane: isopropyl alcohol |
| Flow Rate: | 2.5 mL/min |
| Detector: | 254 nm |
| Diluent: | Sample dissolved in methylene chloride |

Method 2

Using DYNAMAX-60A (Si 83.121-C) preparative HPLC column (30 cm×2.5 cm) with 1:1 of ethyl acetate and hexane as eluant and the flow rate of 10 mL per min, the retention time for 7-α-fluorotaxol was 15.59 min, while the retention time for 8-desmethyl-7,8-cyclopropataxol was 16.65 min.

EXAMPLE 4

7-α-Fluorotaxol (Ia)

Compound IIa (258 mg, 0.26 mmol) was dissolved in THF (1.7 mL) and diethyl ether (3.4 mL), and the solution was cooled to −78° C. To this solution, DAST (69 μL, 0.52 mmol) was added, and the mixture stirred for 30 min at −78° C., and then at room temperature overnight. Water (0.3 mL) was added to quench the reaction and the mixture was concentrated to leave a residue. The residue was purified by silica gel chromatography (being eluted with 30% ethyl acetate in hexane) to give 87 mg (Y: 33.7%) of 2'-O-benzyloxycarbonyl-7-α-fluorotaxol (IIIa) as an amorphous solid. The $^1$H-NMR spectrum was essentially identical to that reported in Example 2; $^{19}$F-NMR (CDCl$_3$) φ(vs. CF$_3$COOH) 90 (ddd, $J_{F,H7}$=49.6 Hz, $J_{F,H6}$=40.1 Hz, $J_{F,H6}$=21.6 Hz).

The removal of 2'-O-benzyloxycarbonyl group as in Example 3 gave the title compound in 87% yield. The $^1$H-NMR was consistent for the structure. HRMS calcd for MH+: 856.3344, found: 856.3367.

EXAMPLE 5

N-Debenzoyl-N-t-butoxycarbonyl-2'-O-triethylsilyl-7-α-fluorotaxol (Va)

A mixture of 7-α-fluorotaxol and 2'-O-benzyloxycarbonyl-8-desmethyl-7,8-cyclopropataxol (572 mg, 3:2 mixture) was treated with tetrabutylammonium borohydride (286 mg, 1.111 mmol) in dry dichloromethane (7 mL) at rt overnight. The excess borohydride was quenched with acetic acid (0.4 mL); the solvent was evaporated to leave a crude product. The crude product thus obtained was purified on a silica gel column (being eluted with 50% ethyl acetate in hexane) to afford 271 mg of a mixture 7-α-fluoro baccatin III (IV) and 8-desmethyl-7,8-cyclopropabaccatin III (XXVII) as a white foam. The NMR spectrum was consistent for the structure.

A solution of the mixture of compound IV and 8-desmethyl-7,8-cyclopropabaccatin III (130 mg) in dry THF (1 mL) was cooled to −40° C. and n-butyllithium (1.63M in hexane, 0.164 mL, 0.260 mmol) was added dropwise under argon. After 15 min, a solution of 1-t-butoxycarbonyl-(3R,4S)-cis-3-triethylsilyloxy-4-phenylazetidinone (XVa) (203 mg, 0.530 mmol) in dry THF (0.5 mL) was added, and the mixture was warmed to 0° C. The reaction was allowed to continue for 90 min at 0° C. and quenched with saturated aqueous ammonium chloride. The reaction mixture was extracted with ethyl acetate. The ethyl acetate layer was dried, filtered and concentrated in vacuo to leave a crude oil. This oil was purified by silica gel chromatography (being eluted with 40% ethyl acetate in hexane) to provide 143 mg of a mixture of title compound and N-debenzoyl-N-t-butoxycarbonyl-2'-O-triethylsilyl-8-desmethyl-7,8-cyclopropataxol (XXVIIIa) as a white foam; $^1$H-NMR (mixture of XXVIIIa and Va, 300 MHz, CDCl$_3$) δ8.14 (d, 2H) 7.45–7.17 (m, 8H) 6.56 (s, 0.6H, H-10) 6.32 (s, 0.4H, H-10) 6.28 (m, 1H, H-13) 5.72 (d, 0.6H, H-2) 5.62 (d, 0.4H, H-2) 5.44 (m, 1H, H-3') 5.28 (exch. m, 1H, N-H) 5.00 (d, 1H, H-5) 4.70–4.45 (m, 1H, H-7) 4.50 (bs, 1H, H-2') 4.40–4.35 (m, 2H, H-20) 4.05 (d, 1H, H-3) 2.63–1.15 (m, 32H) 0.73 (m, 9H) 0.34 (m, 6H).

EXAMPLE 6

N-debenzoyl-N-t-butoxycarbonyl-7-α-fluorotaxol (Ib)

To a solution containing a mixture of compound Va and N-debenzoyl-N-t-butoxycarbonyl-2'-O-triethylsilyl-8-desmethyl-7,8-cyclopropataxol (100 mg) in acetonitrile (1 mL) at −5° C. was added aqueous HCl (0.0192 mL, 0.30 mmol, 36% solution). The reaction mixture was stirred for 10 min and was diluted with ethyl acetate (1.5 mL). The organic phase was washed with water, dried, filtered, and concentrated to leave a residue. The residue was purified by silica gel chromatography (being eluted with 40% ethyl acetate in hexane) to afford 73 mg of a mixture of the title product and N-debenzoyl-N-t-butoxycarbonyl-8-desmethyl-7,8-cyclopropataxol (XXIXa) as a foam; $^1$H-NMR (mixture of XXIXa and Ib, 300 MHz, CDCl$_3$) δ8.11 (m, 2H) 7.60–7.22 (m, 8H) 6.50 (s, 0.6H, H-10) 6.30 (s, 0.4H, H-10) 6.22 (m, 1H, H-13) 5.72 (d, 0.6H, H-2) 5.61 (d, 0.4H, H-2) 5.50–5.42 (m, 1H, H-3') 5.28 (exch. bd, 1H, N-H) 5.00 (d, 1H, H-5) 4.70–4.40 (m, 1H, H-7) 4.60 (bs, 1H, H-2') 4.40–4.23 (m, 2H, H-20) 4.02 (d, 1H, H-3) 3.40 (exch. bs, 1H, O-H) 2.65–1.10 (m, 32H). HRMS Calcd. for MH+ 852.3607, found 852.3604.

EXAMPLE 7

7-α-Fluoro Baccatin II (IV)

To a dry flask under an inert atmosphere was added 2'-O-(benzyloxycarbonyl)taxol (IIa) (4 g, 4 mmol) and dry toluene (80 mL). The resulting slurry was stirred at ambient temperature while dry tetrahydrofuran (16 mL) was added dropwise until a colorless solution resulted. The above solution was cooled to −78° C. in a dry ice/acetone bath then treated with diethylaminosulfur trifluoride (DAST, 1.2 mL, 2.5 eq.). The reaction was allowed to stir for 16h as it gradually warmed to ambient temperature. The resulting suspension was filtered and the filtrate (diluted with ethyl acetate (30 mL)) was washed with saturated aqueous sodium bicarbonate followed by brine. The organic fraction was dried (MgSO$_4$) and concentrated to give a crude product as a white foam. The crude material was partially purified by silica gel column chromatography (eluted with 10% CH$_3$CN in CH$_2$Cl$_2$) to afford 1.45 g of a mixture of the 7-α-fluoro derivative IIIa and 7,8-cyclopropa adduct XXVa (82:18 mixture by $^1$H-NMR).

The above mixture (1.45 g) was taken up in ethyl acetate (60 mL) and treated with palladium on carbon (300 mg). After shaking for 4 h under 50 pounds per square inch (psi) of hydrogen, the reaction was vented and filtered through a short plug of silica gel and concentrated. This furnished the desired product mixture as a white foam (1.24 g, Y: 99%, 90:10 mixture by $^1$H-NMR). The mixture of 7-α-fluoro- and 7,8-cyclopropataxol was taken up in dry methylene chloride (30 mL) and treated with tetrabutylammonium borohydride (745 mg, 2.9 mmol, 2 eq) and allowed to stir for 6 h. The reaction was then quenched with acetic acid (1 mL), diluted with additional methylene chloride (30 mL) and washed with saturated aqueous sodium bicarbonate solution. The organic fraction was dried (MgSO$_4$) and concentrated. The crude, substituted taxane core mixture was partially purified by silica gel column chromatography (eluted with 10% CH$_3$CN in CH$_2$Cl$_2$) to give the title baccatin III (510 mg, 60%) as a 90:10 mixture (as determined by $^1$H-NMR) of 7-α-fluoro and 7,8-cyclopropa analogs as a white foam. The resulting foam was crystallized from hot isopropanol to give 7-α-fluoro baccatin III (IV) as small white needles (Y: 410 mg); m.p. 234°-236° C. (decomposition); $^1$H-NMR (300 MHz, CDCl$_3$): δ8.14 (d, 2H, J=6 Hz), 7.65-7.52 (m, 1H), 7.52-7.49 (m, 2H), 6.57 (s, 1H), 5.72 (d, 1H, J=9 Hz), 5.03 (d, 1H, J=9 Hz), 4.86-4.79 (m, 1H), 4.55 (dd, C-7 proton 1H, J=3.9, J $_{H-F}$=47.1 Hz), 4.36 (A of ABq, 1H, J=7.8 Hz), 4.27 (B of ABq, 1H, J=7.8 Hz), 4.12 (d, 1H, J=6.9 Hz), 2.60- 2.48 (m, 2H), 2.30-1.07 (m, 22H including singlets at 2.30; 2.21; 2.08; 1.77; 1.58; 1.13; 1.07).

EXAMPLE 8

Preparation of
1-t-butoxycarbonyl-(3R,4S)-cis-3-triethylsilyloxy-4-phenylazetidinone (XVa), SCHEME VII (L)-Threonine methyl ester hydrochloride (1.26 g, 7.44 mmol) in anhydrous dichloromethane (15 mL) was stirred with imidazole (1.01 g, 14.89 mmol) and t-butoxydiphenylsilyl chloride (2.274 g, 7.816 mmol) for 16 h at room temperature. The reaction mixture was partitioned between water and dichloromethane. The organic phase was washed with 5% aqueous sodium bicarbonate and water, dried and concentrated to give 2.88 g of a crude oil, which was used directly in the next step; $^1$H-NMR (CDCl$_3$) δ7.70-7.25 (m, 10H) 4.44 (m, 1H) 3.62 (s, 3H) 3.31 (d, J=3 Hz, 1H) 2.12 (bs, 2H) 1.3-1.15 (m, 12H).

The foregoing oil (548 mg, 1.414 mmol) in anhydrous dichloromethane (10 mL) was treated with benzaldehyde (0.158 mL, 1.55 mmol) at rt overnight in the presence of 4 Å molecular sieves to afford compound of formula XVIIa in situ. Upon cooling the solution containing compound XVIIa to −40° C., triethylamine (0.20 mL, 1.698 mmol) was added, followed by acetoxyacetyl chloride (XVIa) (0.182 mL, 1.698 mmol) over 10 min. The mixture was allowed to reach rt over 4 h and the product was partitioned between dichloromethane and water. The organic phase was further washed with water and brine, dried and concentrated. Silica gel chromatography (being eluted with 1:4 EtOAc/hexane) gave 411 mg of compound XVIIIa as a ca. 10:1 mixture of 3R,4S:3S,4R diastereomers.

This mixture of diastereomers (245.1 mg, 0.414 mmol) in dry THF (2 mL) was treated with acetic acid (0.15 mL) and tetrabutylammonium fluoride (TBAF, 1M in THF, 1.20 mL). The solution was stirred for 14 h at rt, then partitioned between ethyl acetate and 5% aqueous sodium bicarbonate. The organic phase was dried and concentrated. Flash silica gel chromatography using 1:1 ethyl acetate/hexane as eluant gave 66 mg (Y: 50%) of compound XIXa (one diastereomer) as a foam; $^1$H-NMR (CDCl$_3$) δ: 7.42-7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

Compound of formula XIXa (9.8 g, 0.0305 mol) in dry dichloromethane (100 mL) was treated at −78° C. with triethylamine (9.40 mL, 0.0671 mol) and methanesulfonyl chloride (MsCl, 3.50 mL, 0.0457 mol). The solution was allowed to reach rt overnight. The reaction mixture was partitioned between water and dichloromethane. The organic layer was washed with 5% aqueous sodium bicarbonate, dilute aqueous HCl, water and brine, and concentrated to afford compound XXa as a crude oily residue. The crude residue (10.0 g) was dissolved in dichloromethane (250 mL) and ozonized at −78° C. until the color of the solution stayed as blue. Addition of methyl sulfide (11 mL) and concentration of the reaction mixture gave compound of formula XXIa (crude).

The compound of formula XXIa was dissolved in THF (150 mL) and treated at −78° C. with hydrazine hydrate (10 mL). After 2 h, the mixture was poured into dilute aqueous HCl and ethyl acetate, and the two phases were separated. The organic phase was washed with more acid, water and brine and concentrated to afford a crude product, which was purified by silica gel chromatography using 1-5% methanol in methylene chloride as eluant to yield 4.40 g (Y: 71%) of compound of formula XXIIa; $^1$H-NMR (CDCl$_3$) δ7.38-7.24 (m, 5H) 6.31 (bs, 1H) 5.87 (bm, 1H) 5.04 (d, J=4.8 Hz, 1H) 1.67 (s, 3H).

To a cooled (−5° C.) mixture of 1M aqueous KOH (140 mL) and acetonitrile (100 mL), a solution of compound XXIIa (2.39 g, 11.22 mmol) in acetonitrile (130 mL) was added dropwise. The mixture was stirred at 0° C. for 1 h and diluted with ethyl acetate (300 mL), water (50 mL) and saturated aqueous bicarbonate (50 mL). The organic phase was separated, and the aqueous layer further extracted with ethyl acetate (3×200 mL). The organic phases were combined, dried, filtered and concentrated to give compound of formula XXIIIa (crude), which was recrystallized from hexane/acetone (mp, 184°-6° C.); yield, 1.53 g (Y: 82%).

To azetidinone XXIIIa (580 mg, 3.55 mmol) in dry THF (5.0 mL) was added imidazole (265.5 mg, 3.90 mmol), followed by triethylsilyl chloride (TESCl, 0.654 mL, 3.90 mmol). The mixture was allowed to be stirred for 1 h. Ethyl acetate was added and the organic layer was washed with brine, 10% aqueous HCl and dried. Silica gel chromatography (being eluted with 25% ethyl acetate in hexane) gave 670 mg (Y: 68%) of compound XXIVa as a foam.

To a stirred solution of compound XXIVa (2.20 g, 7.92 mmol) in dry THF (25 mL) was added diisopropylethylamine (1.65 mL, 9.51 mmol) at 0° C. under argon atmosphere. The solution was stirred for 5 min, then di-t-butylcarbonate (Boc$_2$O, 2.08 g, 9.51 mmol) and 4-dimethylaminopyridine (193.6 mg, 1.58 mmol) were added. The reaction mixture was stirred at 0° C. for 60 min. The reaction was diluted with ethyl acetate (25 mL), and the mixture was washed with brine, 10% aqueous sodium bicarbonate, 10% aqueous HCl, dried over magnesium sulfate, and concentrated to leave an oil. Silica gel flash chromatography (being eluted with 15% ethyl acetate in hexane) gave 2.40 g (Y: 83%) of compound XVa as a white solid; $^1$H-NMR (CDCl$_3$) δ7.28 (m, 5H) 5.03 (m, 2H) 1.38 (s, 9H) 0.76 (t, J=7.56, 9H) 0.43 (m, 6H).

EXAMPLE 9

7-α-Fluoro-2'-O-triethylsilyl-3'-dephenyl-3'-(2-furyl)-N-debenzoyl-N-t-butoxycarbonyltaxol (Vb)

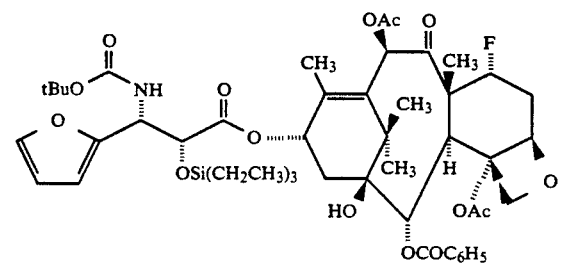

A solution of 7-α-fluoro-baccatin III (IV)(59.3 mg, 0.1 mmol) in dry tetrahydrofuran (5mL) was flushed with an inert atmosphere and cooled to −55° C. in a dry ice/acetone bath. To this solution was added lithium hexamethyldisilazane (0.5M solution in THF, 0.24 mL, 1.2 eq.) dropwise via syringe. The resulting pale yellow solution was allowed to stir for 5 min. Then a tetrahydrofuran (2 mL) solution of the racemic 1-t-butoxycarbonyl-cis-3-triethylsilyloxy-4-(2-furyl)azetidinone (XVb) (178.4 mg, 6 eq.) was added over a 5 min period. The cooling bath was then replaced with an ice/brine bath and the resulting solution allowed to stir at 0° C. for a 1 h period. The reaction was quenched by addition of saturated $NH_4Cl$ solution (2 mL) then was diluted with ethyl acetate (25 mL) and washed with water (2x 10 mL). The organic fraction was dried ($MgSO_4$) and concentrated to give the desired product as a crude colorless oil. The crude product was purified on silica gel using hexanes/ethyl acetate (7:3) as an eluant. This furnished the title product as a colorless glass (80.5 mg, Y: 84%); $^1$H-NMR (300 MHz, $CDCl_3$): δ8.13 (d, 2H, J=9.0 Hz), 7.62–7.56 (m, 1H), 7.51–7.46 (m, 2H), 7.38 (s, 1H), 6.59 (s, 1H), 6.45 (dd, 1H, J=1.8, 3.2 Hz), 6.21 (d, 2H, J=3.2 Hz), 5.76 (d, 1H, J=7.2 Hz), 5.33 (bt, 2H), 5.03 (d, 1H, J=7.5 Hz), 4.75 (s, 1H), 4.57 (dd, C-7 proton 1H, J=4.3, J $_{H-F}$=46.9 Hz), 4.37 (A of ABq, 1H, J=8.4 Hz), 4.27 (B of ABq, 1H, J=8.4 Hz), 4.05 (d, 1H, J=7.2 Hz), 2.49–1.16 (m, 11H, including singlets at: 2.47 (3H), 2.20 (3H), 1.88 (3H), 1.72 (3H), 1.38 (9H)), 0.83 (t, 9H, J=5 Hz), 0.55–0.37 (m, 6H); $^{13}$C-NMR (75.6 MHz, $CDCl_3$): δ206.0, 171.1, 169.4, 169.1, 167.2, 155.2, 152.1, 141.8, 141.4, 133.6, 131.8, 130.1, 129.2, 128.7, 110.6, 107.1, 96.2. 93.9, 81.9, 80.7, 80.0, 78.7, 77.9, 77.8, 75.0, 72.3, 70.8, 56.9, 56.7, 52.7, 42.6. 40.0. 35.5, 33.9, 33.6. 28.1, 28.0, 25.5, 22.5, 21.2, 20.7, 14.6, 14.5. 14.3, 14.2, 6.4, 4.2.

EXAMPLE 10

7-α-Fluoro-2'-O-triethylsilyl-3'-dephenyl-3'-(2-thienyl)-N-debenzoyl-N-t-butoxycarbonyltaxol (Vc)

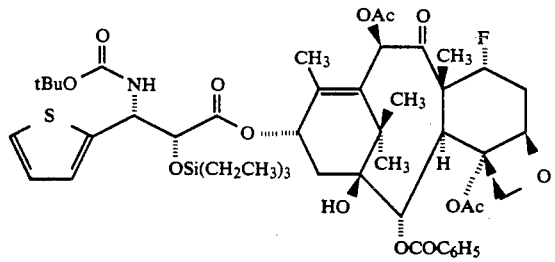

Prepared in the manner described in Example 9 to give the desired product as a white foam (Y: 78% based on recovered starting material); $^1$-NMR (300 MHz, $CDCl_3$): δ8.14 (d, 2H, J=9.0 Hz), 7.63–7.58 (m, 1H), 7.51–7.48 (m, 2H), 7.24 (dd, 2 H, J=2.4,3.6 Hz), 7.00–6.93 (m, 2H), 6.58 (s, 1H), 6.23 (t, 1H, J=9 Hz), 5.77 (d, 1H, J=6 Hz), 5.51–5.42 (m, 2H), 5.03 (d, 1H, J=9 Hz), 4.57 (d, 1H, J=3 Hz), 4.59 (dd, C-7 proton 1H, J=6, J $_{H-F}$=48 Hz), 4.38 (A of ABq, 1H, J=6 Hz), 4.27 (B of ABq, 1H, J=6 Hz), 4.05 (d, 1H, J=7 Hz), 2.57–1.15 (m, 11H, including singlets at: 2.44 (3H), 2.20 (3H), 1.88 (3H), 1.70 (3H), 1.32 (9H)), 0.86 (t, 9H, J=5 Hz), 0.56–0.41 (m, 6H); $^{13}$C-NMR (75.6 MHz, $CDCl_3$): δ206.0, 171.0, 169.4, 168.8, 167.2, 161.4, 142.9, 141.3, 133.6, 131.8, 130.2, 129.2, 128.7, 126.9, 124.6, 124.5, 96.3, 93.9, 81.9, 80.8, 80.0, 78.8, 77.9, 77.8, 77.2, 76.5, 75.2, 75.0, 71.0, 65.4, 56.9 53.7, 42.7, 40.3, 35.6, 33.6, 28.1, 22.7, 21.3, 20.8, 18.8, 14.5, 14.3, 10.4, 6.3, 4.5.

EXAMPLE 11

7-α-Fluoro-3'-dephenyl-3'-(2-furyl)-N-debenzoyl-N-t-butoxycarbonyltaxol (Ie)

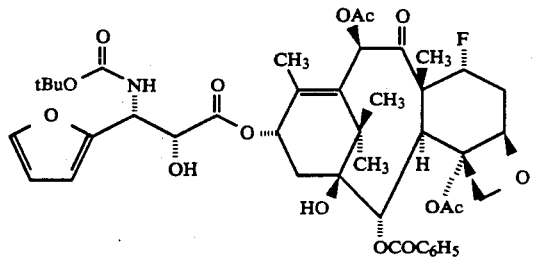

A solution of compound Vb (80 mg, 0.08 mmol) in acetonitrile (2 mL) was cooled to 0° C. in an ice/brine bath. To this solution was added 1N HCl (0.5 mL, 6 eq.) and the reaction was allowed to stir for 30 min at that temperature. The solvent was then evaporated under vacuum and the residue was partitioned between ethyl acetate (25 mL) and water (10 mL). The organic fraction was dried ($MgSO_4$) and concentrated to give a white foam. The crude product was purified on silica gel using 10% $CH_3CN$ in $CH_2Cl_2$ as the eluant. The title product was isolated as a white foam (45.6 mg, Y: 77% based on recovered starting material); $[α]_D$=−26.2° (c 0.8 mg/mL, $CH_2Cl_2$); $^1$H-NMR (300 MHz, $CDCl_3$): δ8.12 (d, 2H, J=6 Hz), 7.63–7.58 (m, 1H), 7.50 (t, 2H, J=6 Hz), 7.41 (s, 1H), 6.57 (s, 1H), 6.37–6.36 (m, 1H), 6.33–6.31 (m, 1H), 6.20 (t, 1H, J=6 Hz), 5.76 (d, 1H, J=6 Hz), 5.37–5.23 (m, 2H), 5.02 (d, 1H, J=9 Hz), 4.71 (bs, 1H), 4.57 (dd, C-7 proton 1H, J=4.2, J $_{H-F}$=46.8 Hz), 4.36 (A of ABq, 1H, J=8.7 Hz), 4.27 (B of ABq, 1H, J=8.1 Hz), 4.04 (d, 1H, J=7.2 Hz), 3.28 (bs, 1H), 2.59–2.20 (m, 5H including singlets at: 2.41 (3H), 2.21 (3H)), 1.85 (s, 3H), 1.43–1.17 (m, 18H); $^{13}$C-NMR (75.6 MHz, $CDCl_3$): δ205.7, 169.2, 169.0, 167.1, 142.3, 140.6, 133.5, 132.1, 130.0, 129.1, 128.6, 110.5, 107.2, 95.9, 93.6, 81.8, 80.6, 78.5, 77.8, 77.7, 74.7, 72.1, 71.6, 56.9, 55.8, 51.5, 42.5, 39.9, 35.4, 33.8, 33.5, 28.0, 27.9, 25.6, 22.2, 20.9, 20.7, 14.5, 14.1, 14.0; HRMS calcd for MH+ ($C_{43}H_{53}NO_{15}F$): 842.3399; Found: 842.3389.

EXAMPLE 12

7-α-Fluoro-3'-dephenyl-3'-(2-thienyl)-N-debenzoyl-N-t-butoxytaxol (If)

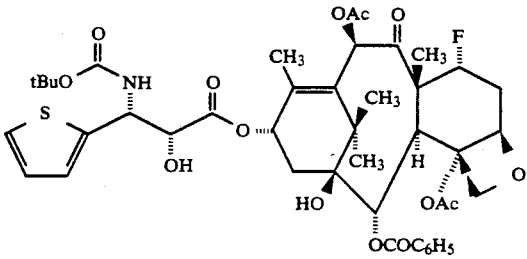

Prepared in the manner described as in Example 11, the title product was isolated as a white foam (22.5 mg, Y: 61%); $^1$H-NMR (300 MHz, $CDCl_3$): δ8.12 (d, 2H, J=9 Hz), 7.64–7.59 (m, 1H), 7.50 (t, 2H, J=9 Hz), 7.28–7.26 (m, 2H), 7.09–7.07 (m, 1H), 7.01–6.98 (m, 1H), 6.56 (s, 1H), 6.19 (t, 1H, J=9 Hz), 5.76 (d, J=6 Hz), 5.53 (bd, 1H, J=12 Hz), 5.35 (d, 1H, J=9 Hz), 5.00 (d, 1H, J=9 Hz), 4.65–4.63 (m, 1.5H, C-7 proton hidden), 4.48 (d, 0.5H, J=9 Hz), 4.36 (A of ABq, 1H, J=8.7 Hz), 4.27 (B of ABq, 1H, J=8.1 Hz), 4.04 (d, 1H, J=7.2 Hz), 3.28 (bs, 1H), 2.59–2.20 (m, 5H including singlets at: 2.39 (3H), 2.18 (3H)), 1.72 (s, 3H), 1.43–1.17 (m, 18H); $^{13}$C-NMR (75.6 MHz, CDCl$_3$): δ205.6, 172.1, 169.3, 169.0, 167.0, 141.5, 140.6, 133.6, 132.1, 130.1, 129.3, 129.0, 128.6, 126.9, 125.2, 125.1, 95.9, 93.5, 81.8, 80.8, 80.2, 78.5, 77.8, 77.7, 77.3, 76.8, 74.7, 73.3, 72.2, 56.9, 52.5, 42.5, 39.9, 35.5, 33.8, 33.5, 28.0, 27.9, 25.6, 22.3, 20.9, 20.7, 11.6, 11.1, 14.0; $[\alpha]_D = -156°$ (c. 0.25 mg/mL, CH$_2$Cl$_2$).

EXAMPLE 13

Preparation of hydrobenzamide, PhCH(—N=CHPh)$_2$

To a 3 L 3-necked flask equipped with a mechanical stirrer and a thermometer was added 1 L of concentrated NH$_4$OH (ca 30%) (14.8 moles). A solution of benzaldehyde (265 g, 2.50 mol) in 500 mL of 2-propanol was added in one portion. The mixture was stirred vigorously at ca 22° C. for 43 hours. The resulting slurry was filtered and the filter cake was washed with water (1 L). After drying in vacuo, 242.4 g of hydrobenzamide was obtained as a white solid (mp 100°–102° C.) for a 97.4% yield.

The above procedure can be followed to prepare the following bis-imines of the formula R$^g$CH(—N=CHR$^g$)$_2$: hydrofuramide (R$^g$=2-furyl) hydrothienamide (R$^g$=2-thienyl)

EXAMPLE 14

(±)-cis-3-Acetyloxy-1-[(phenyl)(benzylidenimino)methyl]-4-phenylazetidin-2-one (XXXVa)

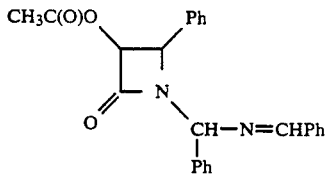

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH$_4$Cl, (sat) (150 mL, 100 mL), aqueous NaHCO$_3$ (saturated) (120 mL) and brine (120 mL). For purposes of characterization, the title compound can be isolated at this stage by drying the organic phase over MgSO$_4$, filtering, and removing the solvent in vacuo. This provided the desired product in quantitative crude yield as a red glass. HPLC purity (area): 87.9% (1:1 mixture of diastereomers); $^1$H-NMR (CDCl$_3$, 200 MHz): δ8.45 (s, 1H, N=CH), 7.80–7.85 (m, 1H, Ph), 7.60–7.65 (m, 1H, Ph), 7.26–7.50 (m, 9H, Ph), 7.00–7.10 (m, 4H, Ph), 6.28 (s, 0.5H, NCHN), 6.23 (s, 0.5H, NCHN), 5.81 (d, J=4.8 Hz, 0.5 H, H-3), 5.76 (d, J=4.8 Hz, 0.5H, H-3), 5.30 (d, J=4.8 Hz, 0.5 H, H-4), 4.75 (d, J=4.8 Hz, 0.5 H, H-4), 1.63 (s, 3H, CH$_3$CO); IR (KBr): ν(cm$^{-1}$)=1763 (C=O), 1641 (C=N); UV (methanol): λmax (nm)=216, 252.

EXAMPLE 5

(±)-cis-3-Acetyloxy-4-phenylazetidin-2-one (XXXVIa)

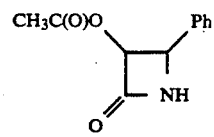

The solution of the compound of Example 14 in ethyl acetate (500 mL) from above was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite ® (diatomaceous earth, Johns Manville). The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine.HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO$_3$ (saturated) (300 mL) and brine (250 mL). The organic layer was dried over MgSO$_4$, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles.

mp=150°–151° C.; HPLC purity (area): 99.8%; $^1$H-NMR (CDCl$_3$, 200 MHz): δ=7.30–7.38 (m, 5H, Ph), 6.54 (bs, exchangeable, 1H, NH), 5.87 (dd, J=2.7, 4.7 Hz, 1H, H-3), 5.04 (d, J=4.7 Hz, 1H, H-4), 1.67 (s, 3H, CH$_3$CO); IR (KBr): ν(cm$^{-1}$)=3210 (N-H), 1755, 1720 (C=O); KF: 0.17%;

Anal. Calcd. for C$_{11}$H$_{11}$NO$_3$: C, 64.38; H, 5.40; N, 6.83. Found: C, 64.07; H, 5.34; N, 6.77.

EXAMPLE 16

(±)-cis-3-Acetyloxy-1-[(2-furyl)(2-furylmethylenimino)methyl]-4-(2-furyl)azetidin-2-one (XXXVb)

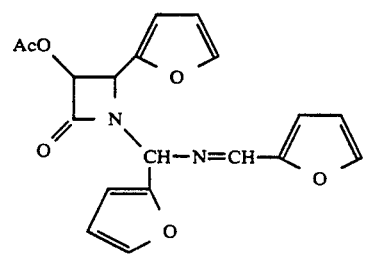

The title compound was prepared according to the procedure described in Example 14 except that hydrofuramide was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (90.4%) of the title compound as a pale red syrup.

Obtained as a 1:1 mixture of diastereomers; $^1$H-NMR (CDCl$_3$; 200 MHz): δ8.211 (s, 0.5H, N=CH), 8.208 (s, 0.5H, N=CH), 7.14–7.59 (m, 3H, furyl), 6.90 (d, J=3.5 Hz, 0.5H, furyl), 6.83 (d, J=3.5 Hz, 0.5H, furyl), 6.10–6.53 (m, 6H, furyl, NCHN), 5.90 (d, J=4.9 Hz, 0.5H, H-3), 5.86 (d, J=4.8 Hz, 0.5H, H-3), 5.35 (d, J=4.8 Hz, 0.5H, H-4), 4.90 (d, J=4.9 Hz, 0.5H, H-4), 1.91 (s, 1.5H, CH$_3$CO),1.88 (s, 1.5H, CH$_3$CO); IR (film): ν(cm$^{-1}$)=1778, 1753 (C=O), 1642 (C=N); UV (methanol): λmax (nm)=220, 278.

EXAMPLE 17

(±)-cis-3-(Acetyloxy)-4-(2-furyl)azetidin-2-one (XXXVIb)

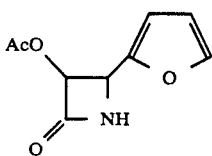

The title compound was prepared according to the procedure described in Example 15 except that the product was isolated by preparative TLC and the reaction was performed on the 2.7 mmol scale based on the original amount of hydrofuramide. Thus, the crude product of Example 16 (1.00 g) was re-dissolved in ethyl acetate (50 mL) and added to 10% palladium on activated charcoal (150 mg). Purification of the crude solid by preparative TLC (2 mm silica gel, 1:1 ethyl acetate/hexane) gave 386 mg (65.8% corrected overall yield from hydrofuramide) of the title compound as a yellow solid. This was recrystallized form ethyl acetate/hexane.

mp=118°–119° C.; HPLC purity (area): 99.4%; $^1$H-NMR (CDCl$_3$, 200 MHz): δ7.44 (t, J=1.3 Hz, 2H, furyl), 6.39 (d, J=1.3 Hz, 1H, furyl), 6.21 (bs, exchangeable, 1H, NH), 5.88 (dd, J=2.2, 4.6 Hz, 1H, H-3), 5.05 (d, J=4.6 Hz, 1H, H-4), 1.92 (s, 3H, CH$_3$CO); IR (KBr): ν(cm$^{-1}$)=3203 (N—H), 1756, 1726 (C=O); UV (methanol): λ max (nm)=222.

EXAMPLE 18

(±)-cis-3-Acetyloxy-1-[(2-thienyl)(2-thienylmethylenimino)methyl]-4-(2-thienyl)azetidin-2-one (XXXVc)

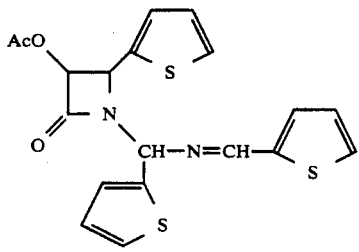

The title compound was prepared according to the procedure described in Example 14 except that hydrothienamide was used instead of hydrobenzamide. Thus, hydrothienamide (30 g, 94.7 mmol), thiethylamine (15.νmL, 114 mmol) and acetoxyacetyl chloride (11.6 mL, 108 mmol) to provide the title compound as viscous oil. The product obtained contained a mixture of diastereomers. $^1$H-NMR (CDCl$_3$): δ8.52 (s, 1H), 8.502 (s, 1H), 7.51 (d, J=4.9 Hz, 1H), 7.45 (d, J=4.4 Hz, 1H), 7.41 (d, J=3.1 Hz, 1H), 7.37 (d, 1H), 7.30 (m, 3H), 7.16 (m, 1H), 7.16 (m, 3H), 7.09 (m, 2H), 6.94 (m, 1H), 6.89 (m, 1H), 6.81–6.74 (m, 4H), 6.48 (s, 1H), 6.43 (s, 1H), 5.85 (m, 2H), 5.59 (d, J=4.8 Hz, 1H), 5.17 (d, J=4.8 Hz, 1H), 1.87 (s, 3H), 1.86 (s, 3H).

EXAMPLE 19

(±)-cis-3-(Acetyloxy)-4-(2-thienyl)azetidin-2-one (XXXVIc)

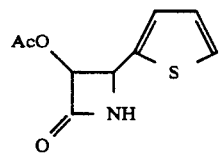

A 70% aqueous solution of acetic acid (0.35 mL glacial acetic acid and 0.15 mL water) was added in one portion to a stirred solution of compound XXXVc (0.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc in hexane provided less polar sideproducts and then the title compound (0.154 g, Y: 75%) as a white solid. $^1$H-NMR (CDCl$_3$): δ7.32 (dd, J=4.7, 1.5 Hz, 1H), 7.03 (m, 2H), 6.75 (bs, 1H), 5.86 (dd, J=4.6, 2.7 Hz, 1H), 5.27 (d, J=5.3 Hz, 1H), 1.83 (s, 3H); $^{13}$C-NMR (CDCl$_3$): δ169.3, 165.5, 138 4, 127.1, 127.07, 126.2, 78.3, 54.0, 20.0.

EXAMPLE 20

7-α-Fluoro-10-desacetyloxytaxol (Ic)

10-Desacetyltaxol VIa (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at rt overnight. The solvent was evaporated and the residue chromatographed on a silica gel column (being eluted with 30–50% ethyl acetate in hexane) to afford 92.3 mg (Y: 46%) of compound XIIIa as a foam. Continued elution also afforded compound VIIa in 16% yield as a foam.

Compound XIIIa (92.3 mg, 0.079 mmol) in dry dichloromethane (2 mL) was treated with 1,1,2-trifluoro-2-chlorotriethylamine (0.0384 mL, 0.238 mmol). The solution was stirred overnight, the solvent evaporated and the residue purified by silica gel chromatography (being eluted with 25% ethyl acetate in hexane) to yield 42.8 mg (Y: 47%) of compound VIIIa as a white solid.

Dienone VIIIa (39 mg, 0.034 mmol) was dissolved in methanol (0.5 mL) and acetic acid (0.5 mL). Zinc dust (66.4 mg, 1.02 mmol) was added, and temperature of the mixture was maintained at 40° C. for 1 h. The insoluble matter was removed by filtration. The filtrate was concentrated and silica gel chromatography of the residue (being eluted with 60% ethyl acetate in hexane) gave 22 mg (Y: 81.5%) of compound IXa as a foam.

Dienone IXa (22 mg, 0.028 mmol) in ethyl acetate (0.7 mL) was hydrogenated at slightly over one atmospheric pressure in the presence of 10% palladium on charcoal (14.7 mg) for 5.5 h at rt. Removal of the catalyst by filtration, and purification of the product by silica gel chromatography (being eluted with 1:1 ethyl acetate/hexane) gave 15 mg (Y: 68%) of compound Xa as a foam.

Compound Xa (27 mg, 0.034 mmol) in dichloromethane (1 mL) was treated with benzyl chloroformate (0.0146 mL, 0.102 mmol), followed by diisopropylethylamine (0.0177 mL, 0.102 mmol). The reaction mixture was stirred at 0° C. for 45 min, and at rt for 12 h. Evaporation of the solvent and silica gel chromatography (being eluted with 40% ethyl acetate in hexane) gave 25.5 mg (Y: 81%) of compound XIa as a foam.

Compound XIa (25.5 mg, 0.028 mmol) in dichloromethane (0.8 mL) at 0° C. was treated with DAST (0.0071 mL, 0.055 mmol). After 45 min at 0° C., the reaction was allowed to proceed for 5 h at rt. Evaporation of the solvent and chromatography gave XIIa as a crude foam. This compound was dissolved in ethyl acetate (1 mL) and was stirred under slightly over one atmosphere of hydrogen in the presence of palladium on charcoal (10%, 8.9 mg) for 12 h at rt. The catalyst was removed by filtration and silica gel chromatography of the product gave 10 mg (Y: 40% over two steps) of compound Ic as a foam; $^1$H-NMR (CDCl$_3$) $\delta$8.08 (d, 2H) 7.70 (d, 2H) 7.68-7.28 (m, 11H) 7.04 (d, 1H) 6.04 (bt, 1H) 5.75 (dd, 1H) 5.69 (d, 1H) 4.92 (d, 1H), 4.72 (dd, 1H) 4.55 (dd, $J_{H,F}$=47 Hz) 4.30–4.21 (m, 3H) 3.81 (dd, 1H) 3.47 (d, exch, 1H) 3.37 (bd, 1H) 2.48–1.30 (m, 13H, incl. singlets at 2.30, 1.72, 1.61) 1.07 (s, 3H) 1.02 (s, 3H); HRMS Calcd for MH+: 798.3290, found, 798.3264.

EXAMPLE 21

7-α-Fluoro-10-desacetyltaxol (Id)

A solution of compound VIIa (obtained as described above, 120 mg, 0 103 mmol) in dichloromethane (2 mL) was cooled at 0° C. and treated with DAST (0.0266 mL, 0.207 mmol). The solution was stirred at 0° C. for 30 min and at rt for 4 h. The reaction was quenched by adding water (0.05 mL). The reaction mixture was concentrated and the residue was purified by silica gel chromatography (being eluted with 30% ethyl acetate in hexane) to afford 81 mg (Y: 68%) of compound XIVa as a foam. This compound (63 mg, 0.054 mmol) was dissolved in methanol (0.5 mL) and acetic acid (0.5 mL) and treated with zinc dust (104 mg, 1.62 mmol) for 90 min at 45° C. The reaction mixture was filtered and the filtrate was concentrated. Silica gel chromatography (being eluted with 40% hexane in 60% ethyl acetate) of the residue afforded 38 mg (Y: 86%) of compound Id as a white solid; $^1$H-NMR (CDCl$_3$) $\delta$8.17 (d, 2H) 7.78 (d, 2H) 7.66-7.26 (m, 11H) 7.15 (d, 1H) 6.20 (bt, 1H) 5.83 (dd, 1H) 5.76 (d, 1H) 5.22 (s, 1H) 5.01 (d, 1H) 4.80 (m, 1H) 4.56 (dd, $J_{H-F}$=47 Hz) 4.40 (m, 2H) 4.10 (d plus exch. s, 2H) 3.55 (d, exch. 1H) 2.66-1.70 (m, 13H, incl. s at 2.41, 1.82, 1.76) 1.12 (s, 3H) 1.03 (s, 3H); HRMS calcd for MH+: 814.3239, found 814.3214.

EXAMPLE 2

(±)- cis-3-Triethylsilyloxy-4-(2-furyl)-azetidin-2-one (XXXVIIa)

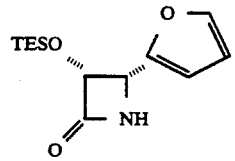

The acetoxy lactam XXXVIb (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47g (Y: 86%) of the title compound as a colorless oil; IR(film) 3276 (broad), 1768, 1184, 732 cm$^{-1}$; $^1$H-NMR (CDCl$_3$, 300 MHz) $\delta$7.38 (s, 1H), 6.39 (bs, 1H), 6.35 (s, 2H), 5.05 (dd, J=4.6, 2.3 Hz, 1H), 4.78 (d, J=4.6Hz, 1H), 0.82 (t,J-8.5 Hz, 6H), 0.50 (dq,J=8.5, 1.8 Hz, 9H); $^{13}$C-NMR (CDCl$_3$, 75.5 Hz) $\delta$169.6, 150.4, 142.6, 110.5, 109.1, 79.6, 53.2, 6.4, 4.4.

EXAMPLE 23

(±)- cis-3-Triethylsilyloxy-4-(2-furyl)-N-t-butoxycarbonylazetidin-2-one (XVb)

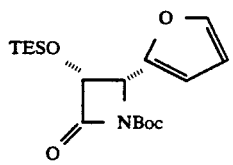

The TES lactam XXXVIIa (2.05 g, 7.7 mmol) in 30 mL of dichloromethane was stirred at 0° C. with diisopropylethyl amine (1.5 mL, 8.6 mmol) and di-t-butylcarbonate (2.0g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 (Y: 70%) of the title compound as a waxy solid.

EXAMPLE 24

(±)-cis-3-Triethylsilyloxy-4-(2-thienyl)-azetidin-2-one (XXXVIIb)

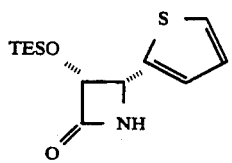

A solution of 3-acetoxy lactam XXXVIc (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1 7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give the desired product as a colorless solid (1.5 g, Y: 45%). m.p. 70°–71° C.; $^1$H-NMR (300 MHz, CDCl$_3$): δ7.32–7.30 (m, 1H); 7.05–6.98 (m, 2H), 5.06–5.05 (m, 2H), 0.82 (t, 9H, J=8 Hz), 0.55–0.46 (m, 6H); $^{13}$C-NMR (75.6 MHz, CDCl$_3$): δ169.1, 139.7, 126.5, 126.4, 125.8, 79.4, 55.1, 6.3, 4.4.

EXAMPLE 25

(±)-cis-3-Triethylsilyloxy-4-(2-thienyl)-N-t-butoxycarbonylazetidin-2-one (XVc)

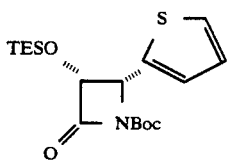

A solution of the silyl azetidinone XXXVIIb (425.7 mg, 1.48 mmol) was dissolved in dichloromethane (10 mL) and cooled to 5° C. in an ice/water bath. The reaction was treated with a catalytic amount of DMAP followed by diisopropylethylamine ( 0.25 mL, 1.0 eq) then di-t-butylcarbonate (388.4 mg, 1.2 eq). After stirring 2 h at that temperature the reaction was quenched with saturated aqueous sodium bicarbonate (5 mL) and the organic fraction was washed with water (5 mL) then dried (MgSO$_4$), passed through a short plug of silica gel and concentrated to give the desired product as a colorless oil (525.3 mg, Y: 93%); $^1$H-NMR (300 MHz, CDCl$_3$): δ7.31–7.29 (m, 1H), 7.08–7.07 (m 1H), 7.00–6.58 (m, 1H), 5.31 (d, 1H, J=6 Hz), 5.03 (d, 1H, J=6 Hz), 1.40 (s, 9H), 0.83 (t, 9H, =8 Hz), 0.56–0.47 (m, 6H); $^{13}$C-NMR (75.6 MHz, CDCl$_3$): δ165.5, 147.5, 136.4, 127.6, 126.2, 126.1, 83.3, 77.3, 57.9, 27.7, 6.2, 4.3.

EXAMPLE 26

Following the processes and Examples described herein, the following specific taxol derivatives of formula I can be synthesized:

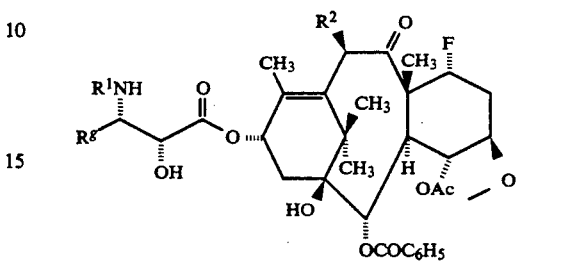

7-α-Fluoro-3'-dephenyl-3'-(2-thienyl)taxol (R$^g$=2-thienyl, R$^1$=benzoyl, R$^2$=OAc)

7-α-Fluoro-3'-dephenyl-3'-(2-furyl)taxol (R$^g$=2-furyl, R$^1$=benzoyl, R$^2$=OAc)

7-α-Fluoro-10-desacetyl-10-benzoyl-3'-dephenyl-3'-(2-furyl)taxol (R$^g$=2-furyl, R$^1$=benzoyl, R$^2$=—OCOC$_6$H$_5$)

7-α-Fluoro-10-desacetyl-10-benzoyl-3'-dephenyl-3'-(2-thienyl)taxol (R$^g$=2-thienyl, R$^1$=benzoyl, R$^2$=—OCOC$_6$H$_5$)

7-α-Fluoro-10-desacetyl-10-methyl-3'-dephenyl-3'-(2-thienyl)taxol (R$^g$=2-thienyl, R$^1$=benzoyl, R$^2$=OCH$_3$)

7-α-Fluoro-10-desacetyl-10-phenylmethylcarbonyl-3'-dephenyl-3'-(2-furyl)taxol (R$^g$=2-furyl, R$^1$=benzoyl, R$^2$=—OC(=O)OCH$_2$C$_6$H$_5$)

7-α-Fluoro-10-desacetyl-10-n-butylcarbonyl-3'-dephenyl-3'-(2-thienyl)taxol (R$^g$=2-thienyl, R$^1$=benzoyl, R$^2$=OCOCH$_2$CH$_2$CH$_2$CH$_3$)

7-α-Fluoro-10-desacetyl-10-methylsulfonyl-3'-dephenyl-3'-(2-furyl)taxol (R$^g$=2-furyl, R$^1$=benzoyl, R$^2$=—OSO$_2$CH$_3$)

EXAMPLE 27

Representative example to derivatize, selectively, the C-10 position of 10-desacetylbaccatin 10-Benzoyl-10-desacetyl-7-triethylsilylbaccatin (XXXIXa)

Under argon atmosphere, the baccatin derivate of formula XXXVIII in which R$^3$ equals SiEt$_3$ (43.5 mg, 0.066 mmol) was dissolved in dry tetrahydrofuran (1.0 mL). The solution was cooled to −40° C. and n-BuLi (0.050 mL, 0.82 mmol, 1.6 M solution) was added slowly. After 5 minutes of stirring, benzoyl chloride (0.030 mL, 0.26 mmol) was added and the reaction mixture was warmed to 0° C. The reaction mixture was stirred for 1.5 h before quenching into a saturated solution of ammonium chloride (2 mL). The aqueous medium was extracted with ethyl acetate (2×5 mL), dried (magnesium sulfate), and evaporated to afford an oil. Flash silica gel chromatography (eluted with 50% ethyl acetate in hexanes) afford the title compound (30 mg, Y: 60%, a compound of formula XXXIX in which R$^3$=Si(Et)$_3$, R$^m$=OCOC$_6$H$_5$) as a foam; $^1$H-NMR (CDCl$_3$): δ 8.17–8.05 (m, 4H), 7.64–7.42 (m, 6H), 6.67 (s, 1H), 5.67 (d, 1H), 4.95 (d, 1H), 4.81 (m, 1H), 4.56 (dd, 1H), 4.30 (d, 1H), 4.14 (d, 1H), 3.92 (d, 1H), 2.50 (m, 1H), 2.30–2.0 (m, 18H), 1.92–1.80 (m, 1H), 1.72–1.62 (bs, 4H), 1.30 (s, 3H), 1.00 (s, 3H), 0.89 (t,3H), 0.56 (q, 6H); HRMS (FAB/NOBA): Calculated for $C_{42}H_{54}O_{11}$-Si(MH+): 762.3435. Found 762.3427.

Using this methodology, C-10 carbonates, sulfonates, carbamates, ethers, etc., can be prepared. Yields will be found better when lithium hexamethyldisilazane is employed.

BIOLOGICAL DATA

In Vitro Cytotoxicity Data

The 7-fluorotaxol derivatives of the present invention showed in vitro cytotoxicity activity against human colon carcinoma cells HCT-116 and HCT-116/VM46. The HCT-116/VM46 cells are cells that have been previously selected for teniposide resistance and express the multi-drug resistance phenotype, including resistance to taxol. Cytotoxicity was assessed in HCT-116 human colon carcinoma cells by XTT (2,3-bis(2-methoxy-4-nitro- 5-sulfpphenyl)-5[(phenylamino)carbonyl]2H-tetrazolium hydroxide) assay as reported in D.A. Scudiero, et al., "Evaluation of soluble tetrazolium/formazan assay for cell growth and drug sensitivity in culture using human and other tumor cell lines," *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for compounds evaluated in this assay are given in Table I.

TABLE I

| | In vitro cytotoxicity data against human colon carcinoma cells. | |
|---|---|---|
| | $IC_{50}$ (μM) | |
| Compound | HCT-116 | HCT-116/VM46 |
| Ic | 0.301 | 0.979 (3.3)* |
| Id | 0.053 | 1.30 (25) |
| Ia | 0.011 | 0.158 (14) |
| taxol | 0.004 | 0.440 (124) |

*Value is parenthesis is fold resistance relative to HCT-116 cells.

Mice M109 Model

Balb/c×DBA/2 $F_1$ hybrid mice were implanted intraperitoneally, as described by William Rose in Evaluation of Madison 109 Lung Carcinoma as a Model for Screening Antitumor Drugs, *Cancer Treatment Reports*, 65, No. 3–4 (1981), with 0.5 mL of a 2% (w/v) brei of M109 lung carcinoma.

Mice were treated with compound under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C) in Table II for a representative compound.

TABLE II

| IP M109 data | |
|---|---|
| Compound | % T/C (dose in mg/kg/injection: schedule) |
| Ib | 147 (40; d. 5 + 8) |

The compounds of formula I invention have tumor inhibiting activities in mammals. Thus, another aspect of the instant invention concerns a method for inhibiting mammalian tumors sensitive to a compound of formula I. The present invention also provides intermediates useful for making 7-fluoro taxol derivatives of formula I.

The compounds of formula I can also be used to make water soluble prodrugs. A number of water soluble prodrugs of taxol have been described. See for example, U.S. Pat. No. 5,059,699, issued to Kingston et al on Oct. 22, 1991; U.S. Pat. No. 4,942,184, issued to Haugwitz et al on Jul. 17, 1990; U.S. Pat. No. 4,960,790, issued to Stella et al on Oct. 2, 1990; all three U.S. patents are hereby incorporated by reference in their entirety. The water solubilizing moieties described in the aforementioned three U.S. patents can also be linked to the 2'- and/or 10-hydroxy group of a compound of formula I to make it more water soluble. Thus this invention provides antitumor compounds which can be used to make prodrugs thereof.

The present invention also provides pharmaceutical compositions (formulations) containing a compound of formula I in combination with one or more pharmaceutically acceptable, inert or physiologically active, carriers, excipients, diluents or adjuvants. Examples of formulating taxol or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of the present invention can be used in substantially the same manner as taxol in treating mammalian tumors. The mode, dosage and schedule of administration of taxol in human cancer patients have been extensively studied. See, for example *Ann. Int. Med.*, 111, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m² of the patient. An oncologist skilled in the art of cancer treatment will able to ascertain, without undue experimentations, appropriate protocols for effective administration of the compounds of this present invention by referring to the earlier studies of taxol and its derivatives.

What is claimed is:

1. A compound of formula I

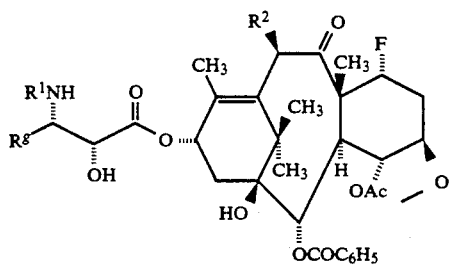

in which $R^1$ is —$COR^z$ in which $R^z$ is RO— or R;

$R^g$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^2$ is —OCOR, H, OH, —OR, —$OSO_2R$, —OCON$R^oR$, —OCONHR, —OCOO$(CH_2)_tR$, or —OCOOR; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

2. A compound of claim 1 in which $R^1$ is t-butoxycarbonyl or $C_6H_5CO$—; $R^2$ is —$OCOCH_3$, H, or OH; and $R^g$ is phenyl, 2-thienyl or 2-furyl.

3. A compound of claim 2 that is 7-α-fluorotaxol.

4. A compound of claim 2 that is N-debenzoyl-N-t-butoxycarbonyl-7-α-fluorotaxol.

5. A compound of claim 2 that is 7-α-fluoro-10-desacetyloxytaxol.

6. A compound of claim 2 that is 7-α-fluoro-10-desacetyltaxol.

7. A compound of claim 2 that is 7-α-fluoro-3'-dephenyl-3'-(2-furyl)-N-debenzoyl-N-t-butoxycarbonyltaxol.

8. A compound of claim 2 that is 7-α-fluoro-3'-dephenyl-3'-(2-thienyl)-N-debenzoyl-N-t-butoxycarbonyltaxol.

9. A compound of claim 2 that is 7-α-fluoro-3'-dephenyl-3'-(2-thienyl)taxol.

10. A compound of claim 2 that is 7-α-fluoro-3'-dephenyl-3'-(2-furyl)taxol.

11. A pharmaceutical formulation which comprises as an active ingredient a compound as claimed in any one of claims 1 to 10 associated with one or more pharmaceutically acceptable carriers, excipients or diluents therefor.

12. A method for treating mammalian tumors which comprises administering to a mammal a tumor sensitive amount of a compound as claimed in any one of claims 1 to 10.

13. The fluorobaccatin III of formula IV

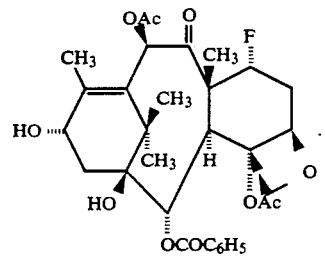

* * * * *

UNITED STATES PATENT AND TRADEMARK OFFICE
CERTIFICATE OF CORRECTION

PATENT NO. : 5,294,637            Page 1 of 2
DATED : March 15, 1994
INVENTOR(S) : Shu-Hui Chen, et al It is certified that error appears in the above-indentified patent and that said Letters Patent is hereby corrected as shown below:

In the claims:

Column 37 of taxane structure of formula I

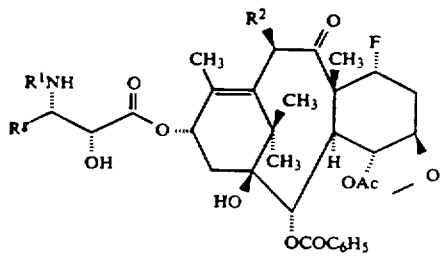 should read 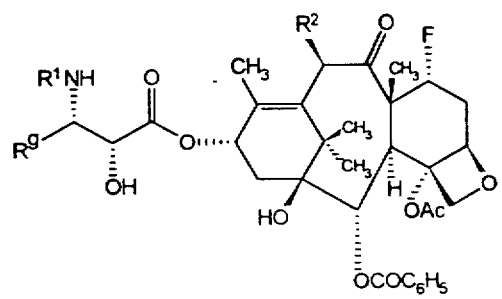

and column 38 of taxane stucture of formula IV

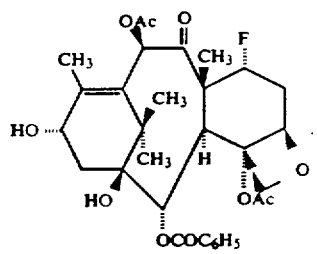 should read 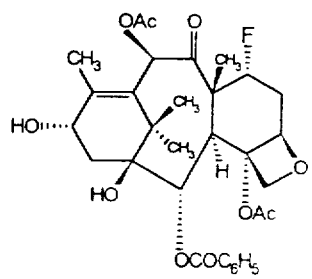

UNITED STATES PATENT AND TRADEMARK OFFICE
CERTIFICATE OF CORRECTION

PATENT NO. : 5,294,637
DATED : March 15, 1994
INVENTOR(S) : Shu-Hui Chen, et al

It is certified that error appears in the above-indentified patent and that said Letters Patent is hereby corrected as shown below:

Likewise, the same errors in the structural formulas of taxanes appear throughout the entire specification; thus all taxane structures should contain an oxetane ring with C(4) and C(5) carbons being a part of the oxetane ring.

Signed and Sealed this

Twenty-sixth Day of July, 1994

Attest:

BRUCE LEHMAN

Attesting Officer

Commissioner of Patents and Trademarks